United States Patent
Hoeffkes et al.

(10) Patent No.: US 7,225,920 B2
(45) Date of Patent: Jun. 5, 2007

(54) MIXING DEVICE

(75) Inventors: Horst Hoeffkes, Duesseldorf (DE); Ullrich Bernecker, Aachen (DE); Martina Seiler, Duisburg (DE)

(73) Assignee: Henkel Kommanditgesellschaft auf Aktien, Dusseldorf (DE)

( * ) Notice: Subject to any disclaimer, the term of this patent is extended or adjusted under 35 U.S.C. 154(b) by 5 days.

(21) Appl. No.: 11/222,564

(22) Filed: Sep. 9, 2005

(65) Prior Publication Data

US 2006/0002965 A1  Jan. 5, 2006

Related U.S. Application Data

(63) Continuation of application No. PCT/EP2004/002694, filed on Mar. 16, 2004.

(30) Foreign Application Priority Data

Mar. 22, 2003 (DE) ................. 103 12 895
Mar. 3, 2004  (DE) ............. 10 2004 010 975

(51) Int. Cl.
 *B01F 3/12* (2006.01)
 *B01F 13/00* (2006.01)
 *B01F 15/02* (2006.01)
 *B65D 65/46* (2006.01)

(52) U.S. Cl. ...................... 206/222; 366/130

(58) Field of Classification Search ............... 366/130; 206/222, 219; 383/200
See application file for complete search history.

(56) References Cited

U.S. PATENT DOCUMENTS 58,882 A * 10/1866 Pinder ................. 366/130
1,075,119 A * 10/1913 Reichner ................. 99/508
1,332,985 A *  3/1920 Jarrett .................. 206/222
1,748,483 A *  2/1930 Hyde .................... 99/508
2,500,611 A *  3/1950 Kereluck ................. 99/508
2,592,485 A    4/1952 Stair
2,618,143 A * 11/1952 McConaughy ............ 68/213
3,339,802 A *  9/1967 Weiner et al. ............ 222/82
3,347,410 A * 10/1967 Schwartzman ........... 222/80
3,548,562 A * 12/1970 Schwartzman ........... 53/440
3,786,820 A *  1/1974 Kopfer ................. 132/74.5
3,802,272 A *  4/1974 Bischoff et al. .......... 73/866
4,003,555 A *  1/1977 Swartz ................. 366/130
4,177,938 A * 12/1979 Brina .................... 222/80
4,193,698 A *  3/1980 Gartner ................. 366/130

(Continued)

FOREIGN PATENT DOCUMENTS

DE  1 053 739  9/1957

(Continued)

*Primary Examiner*—Tony G. Soohoo
(74) *Attorney, Agent, or Firm*—Paul & Paul

(57) ABSTRACT

The invention relates to a mixing device for mixing a pulverulent product, which is contained in a film sachet that is soluble in liquid, with said liquid and optionally at least one additional component. The aim of the invention is to accelerate the mixing of pulverulent products, which are packed in film sachets that are soluble in liquid, with a liquid, without the risk of creating dust. This is achieved by a sealable mixing container (2) comprising a receiving chamber (7) for the pulverulent product (9) contained in the film sachet (8), the liquid and the optional additional component. The receiving chamber (7) is equipped with fitted components (6, 6'), which act mechanically on the film sachet (8).

20 Claims, 1 Drawing Sheet

U.S. PATENT DOCUMENTS

| | | | |
|---|---|---|---|
| 4,808,006 A * | 2/1989 | Kaufeler | 366/332 |
| 5,063,057 A | 11/1991 | Spellman | |
| 5,116,388 A | 5/1992 | Brooks | |
| 5,154,321 A * | 10/1992 | Shomer | 222/129 |
| 5,270,054 A | 12/1993 | Bertolini | |
| 5,484,598 A | 1/1996 | Schurig | |
| 5,788,369 A | 8/1998 | Tseng | |
| 6,187,058 B1 | 2/2001 | Massoni | |
| 6,365,136 B1 | 4/2002 | Lauscher | |
| 6,485,528 B1 | 11/2002 | Bartels | |

FOREIGN PATENT DOCUMENTS

| | | |
|---|---|---|
| DE | 42 17 920 | 12/1993 |
| DE | 196 13 941 | 10/1997 |
| DE | 199 09 661 | 9/2000 |
| DE | 100 59 291 | 6/2002 |
| EP | 0 479 404 | 4/1992 |
| EP | 1 308 151 | 5/2003 |
| GB | 130548 | 8/1919 |
| GB | 666244 | 2/1952 |
| GB | 2 118 961 | 11/1983 |
| GB | 2 356 842 | 6/2001 |
| WO | WO 95/11861 | 5/1995 |
| WO | WO 99/30673 | 6/1999 |

* cited by examiner

MIXING DEVICE

CROSS REFERENCE TO RELATED APPLICATIONS

This application is a §365(c) continuation application of PCT/EP2004/002694 filed Mar. 16, 2004, which in turn claims priority to DE Application 103 12 895.6 filed Mar. 22, 2003 and DE Application 102004010975.3 filed Mar. 3, 2004, each of the foregoing applications is incorporated herein by reference.

FIELD OF THE INVENTION

The invention relates to a mixing device for mixing a piece-form, gel-like, pasty, pulverulent, liquid product or the like, which is contained in a film sachet which is soluble in a liquid solvent, with the liquid solvent and optionally at least one further component.

BACKGROUND OF THE INVENTION

In the case of pulverulent cosmetic products which, in order to be used, have to be converted to a liquid-based, in particular water-based, form, for example, it must be ensured that when converting the pulverulent product into the liquid solvent a risk of creating dust for the user does not, as far as possible, take place. Such a risk of creating dust is particularly undesirable and to be avoided if the pulverulent products are strongly acidic, strongly alkaline or chemically active, such as, for example, bleaching powder.

To avoid dust formation, granulation processes have, inter alia, been proposed, for bleaching powders in particular dedusting with oil components. However, besides impaired miscibility of the powder with the liquid components prior to use, these granulation processes with oxidizable components also harbor potential risks, e.g. with regard to reduced storage stability due to the simultaneous presence of oxidizing and oxidizable components. Sometimes, the formulation of components which may be subject to hydrolysis (or in some cases solvatolysis in polar solvents) in oil-based formulations is also of interest.

It has already been proposed to package bleaching powder in a water-soluble film sachet. The powder is then placed in the film sachet into a liquid solvent, the film sachet gradually dissolves and mixing of the powder with the liquid solvent can take place. In practice, however, the delayed solubility of the film sachet has proven to be disadvantageous, i.e. the preparation time is too long and unacceptable for the user.

An object of the invention is therefore to overcome the disadvantages of the prior art. This object is achieved using a mixing device with the features of the present invention. Through a sealable mixing container with a receiving chamber for the product contained in the film sachet and the liquid solvent and the optional further components, internal inserts for the mechanical destruction of the film sachet being provided in the area of the receiving chamber. Here, the mixing mechanism can be used for all aggregate states of the product, in particular piece-form, gel-like, pasty, pulverulent, liquid or the like.

Using such a mixing device, it is possible, after introducing the components and sealing the mixing container, to mechanically destroy and/or to comminute the film sachet containing the pulverulent product, which leads to accelerated dissolution of the film and to a significantly shortened mixing time of the product with the remaining components. Here, the internal inserts in the receiving chamber of the mixing container can in principle be of varying designs where, in the case of the simplest configurations in terms of construction, it is possible to make the internal inserts effective in a simple manner by the mixing device being shaken by the user, which is in any case sensible and useful for increasing the rate of the mixing operation per se.

In order to make the device easier to handle when opening and closing it, it is advantageously provided that the mixing container has a container opening which is sealable by a removable lid. The components to be mixed can then, after the lid has been removed, simply be introduced into the receiving chamber of the mixing container, then the lid can be put back on again.

It is particularly expedient if the internal inserts are formed as an insert arranged in the area of the container opening. After the mixing operation and opening of the container lid, the insert can then be removed from the area of the container opening and the product obtained after mixing can be removed from the container without problems.

According to a first advantageous configuration, it is envisaged that the insert is designed like a lemon squeezer toward the receiving chamber.

Alternatively, it can also be envisaged that the insert is designed like a sieve plate with tapered pins or spikes pointing into the receiving chamber. Furthermore, it can also be envisaged to equip the insert with knife-like elements pointing inwards. In addition, all of the combinations of the specified inserts or others can be envisaged. The film sachet advantageously consists of polyvinyl alcohol or gelatin, but generally of a solid which is soluble in the added liquid solvent to be mixed.

In an advantageous configuration, it is envisaged that the product is a bleaching powder and the liquid solvent is a hydrogen peroxide solution. The mixing device can then be used to prepare a bleaching composition. The further component here is then advantageously a bleaching cream.

The invention also proposes a mixing set with an above-described device and a product contained in a film sachet soluble in a liquid solvent, optionally a receiving container filled with the liquid solvent, and optionally a receiving container filled with a further component.

Cosmetic Portion

In an advantageous embodiment of the present invention, the mixing set according to the invention includes a cosmetic portion. This portion consists of a coating soluble in a liquid solvent, in particular a corresponding film sachet, and a product contained therein.

The set object is achieved in this embodiment according to the invention through the mechanical action in the mixing device and through the specific shape of the film sachet.

In the field of cosmetics, there is a great need for products which should on the one hand be effective and on the other hand should be simple and above all safe for the consumer to handle and use. In the field of hair cosmetics in particular, bleaching and hair-dyeing systems have developed in recent years which are extremely effective but, if handled improperly, for example in cases of contamination with areas of skin or eyes, can lead to irritations or, in extreme cases, even to allergies being triggered. There was therefore a great need to ensure the safety of the handling of such cosmetic formulations and, moreover, to give the consumer a packaging system which is easy to dose by hand and which also allows a mixing or a combining of the required components on site by the consumer.

The prior art already discloses water-soluble sachet-packaged hair cosmetic formulations. DE 196 13 941 A1 describes a method for the preparation of nondusting pulverulent compositions for the bleaching of human hair. The blonding compositions have at least one peroxide compound, which are admixed with suitable thickeners and then packaged in portions in water-soluble sachets for transportation and further processing.

EP-A1-1037589 discloses a composition for the treatment of keratin fibers, consisting of at least one aqueous preparation A and at least one spatially separate preparation B which comprises a constituent which is not storage-stable in preparation A, chosen from the group which is formed by perfume oils, and vitamins, provitamins and derivatives thereof, where the film sachet with preparation B of a material which, when preparation B is added to preparation A, allows a mixing of the components of both preparations at 38° C. within 5 minutes.

U.S. Pat. No. 5,116,388 discloses hair colorants based on oxidation dyes, and bleaches for bleaching hair which are incorporated into polyvinyl alcohol packaging in order to prevent the irritations caused by powder dust.

Although the portioned cosmetic formulations disclosed in the prior art offer improved handleability and a reduction in the dust contamination of the packaged cosmetic preparations, the portions packaged in water-soluble film systems have the disadvantage that they dissolve only slowly in water. Moreover, the water-soluble cosmetic portions disclosed in the prior art, especially in the field of hair cosmetics, have the disadvantage that the portions can slide out of the consumer's hands and possibly burst. It is not uncommon for consumers who use hair cosmetic products to have wet hands or fingers, for example because the hair has been washed just before application, which increases to an extreme degree the risk of cosmetic portions slipping off. Many of the cosmetic individual portions disclosed in the prior art are often sold in a further water-impermeable secondary packaging. The secondary packagings often consist here of smooth film sachets or metal-coated smooth packaging systems, so that the water-soluble PVA cosmetic portions described in the prior art lie flat against the surfaces of the secondary packaging materials and, due to high adhesion forces, do not slide easily out of the secondary packaging container. An object of the embodiment according to the invention is to provide portioned cosmetic preparation in water-soluble and/or water-dispersible film sachets which do not have the abovementioned problems of the prior art.

SUMMARY OF THE INVENTION

It has been found that the abovementioned problems are solved by the special configuration of a portion.

A portion comprising a cosmetic preparation and a water-soluble and/or water-dispersible film sachet, where this film sachet covers the cosmetic preparation and the surface of the film sachet has a square mean value for the roughness of at least 10 μm.

These portions have cosmetic preparations which are covered by water-soluble and/or water-dispersible film sachets. However, film sachets which are completely soluble in water are advantageous. Within the scope of the present embodiment according to the invention, the term "portion" or "cosmetic portion" is used synonymously with the term "portioned cosmetic preparation in water-soluble and/or water-dispersible film sachets". The portions of the embodiment according to the invention have a film sachet whose surface advantageously has a square mean value for the roughness of at least 10 μm. Preferably, the surface of the film sachet has a square mean value for the roughness of from 10 to 100 μm, particularly advantageously from 10 to 50 μm and in particular from 30 to 35 μm. Within the scope of this embodiment, the term "surface" refers to the flat areas of the film sachet, for example of a polymer film.

The square mean value for the roughness of the film sachet was determined in accordance with DIN 4762/1 using standard commercial surface scanning devices.

Film sachet materials based on polyvinyl alcohol, for example as polymer films which have the roughness values given above are commercially available, from Syntana under the trade name Solublon® PVAL film, type SA 20.

As a result of the fact that the film sachets to be used according to the invention have a significantly rougher surface compared to the film sachets used in this field in the prior art, the three-dimensional macroscopic surface of the film sachet also increases in size. The three-dimensional macroscopic surface additionally takes into consideration the areas which are stretched due to irregularities on the film surface. For the case of an ideally smooth surface, the three-dimensionally macroscopic surface corresponds to the two-dimensional geometric surface. In a further embodiment, the three-dimensional macroscopic surface of the film sachet of the portion is at least 10%, advantageously at least 20%, further advantageously between 20 and 100%, extremely advantageously between 30 and 50%, larger than the two-dimensional geometric surface.

The present embodiment according to the invention thus provides portions comprising a cosmetic preparation and a water-soluble and/or water-dispersible film sachet, where the film sachet covers the cosmetic preparation and the three-dimensional macroscopic surface of the film sachet of the portion is at least 10%, advantageously at least 20%, further advantageously between 20 and 100%, most advantageously between 30 and 50%, larger than the two-dimensional geometric surface.

The three-dimensional surface is determined starting from the reference surface which has the shape of the geometric surface and agrees in terms of its position within the chamber with the main direction of the actual surface.

The three-dimensional macroscopic surface, which is larger than the two-dimensional geometric surface, contributes, inter alia, to an improved solubility in water of the portions according to the invention.

With the portions according to the invention, it is advantageous that at least one surface of the film sachet has a three-dimensional structure, preferably an embossed three-dimensional structure.

The outer surface and/or inner surface of the film sachet can here be provided to at least 50%, preferably at least 70%, further advantageously at least to 90% and in particular essentially completely, with a three-dimensional, preferably embossed, structure.

In the course of the present embodiment according to the invention, the inner surface of the film sachet refers to the flat area which can be in contact with the cosmetic preparation. In the case of the presence of a film sachet, the surface of the film in the inside of the sachet is thus the inner surface and the film surface outside of the inside of the sachet is the outer surface. The outer surface is not in contact with the cosmetic preparation of the portion according to the invention.

In an advantageous embodiment, the structure embossed on a surface of the film sachet is a regular embossed three-dimensional structure in the form of a pattern.

In one advantageous embodiment, the embossed structure has, on the surface, a regular three-dimensional pattern. The regular pattern can here have any imaginable shape, for example squares, rhomboids, punched-in cylinders, ovals, etc. In one advantageous embodiment, the regular pattern consists in a periodically repeating arrangement of raised areas and indentations of the film sachet surface.

The embossed pattern can here influence both the haptic properties of the portion according to the invention and also its dissolution rate. It has therefore proven to be advantageous that the embossed pattern has at least 4, preferably at least 6, particularly advantageously between 8 and 50, further advantageously between 10 and 25, indentations or raised areas per 1 cm$^2$ of the two-dimensional surface. Embossed indentations or raised areas have, within the scope of the present embodiment according to the invention, in their greatest extension at least a diameter of 2 µm and a depth or height of at least 2 µm, preferably at least 5 µm.

In a further advantageous embodiment, the surface of the film sachet has circular and/or triangular and/or rectangular and/or polygonal indentations.

In a further embodiment, the surfaces of the film sachet can, however, also have parallepiped, round, angular, oval sawtooth-shaped or raised areas triangularly tapering toward the surface.

In one advantageous embodiment, the surface of the film sachet has a grid-like or honeycomb-like three-dimensional structured pattern. These patterns are preferably embossed or stamped onto the coating surface and thus give the surface a three-dimensional profile. In one advantageous embodiment, the film sachet has grid lines as a result of embossing a grid-like or honeycomb-like pattern. The grid lines are advantageously formed by a stringing together of edges limiting the indentations.

The advantageous grid-like patterns are preferably embossed onto the surfaces of the film sachet such that the ratio of the average width of grid line to the maximum extension of the plane of the indentation is less than 20:1, preferably less than 10:1, particularly advantageously less than 1:1, further advantageously less than 0.5:1 and in particular less than 0.25:1.

In the case of embossed patterns in particular, it has proven to be advantageous that the ratio of average diameter of the indentation to the depth of the indentation is less than 20:1, preferably 10:1 to 1:10, in particular 8:1 to 1:1, specifically 6:1 to 4:1.

The portions according to the invention can have film sachets which have an embossed three-dimensional pattern on only one side, in particular only on the outside of the coating surface which is not in contact with the cosmetic preparation. However, it is advantageous for the film sachets to have an embossed three-dimensional structured pattern on both sides, i.e. for both the inside and the outside of the film sachet to bear this pattern.

Preferably, the portions according to the invention have film sachets whose average thickness is 10 to 100 µm, preferably 15 to 50 µm and in particular 20 to 40 µm. The chosen film sachet thicknesses contribute, particularly when the film sachets are water-soluble and/or water-dispersible films, to an optimum dissolution rate in water and additionally to good processing of the films. Thus, it has been found that, particularly in the range of an average film thickness between 10 and 100 µm, that thermal sealing, in particular liquid-tight sealing, can be carried out without problems. The film thickness can here relate to partial areas or advantageously to the entire coating material. The average film thickness refers to the cross section profile and was averaged over the raised areas and indentations along a profile section 1 cm in length. A section of film 1 square centimeter in size (1 cm×1 cm) of the coating material is divided into 5 equal strips (each 2 mm) and in each case the average film thickness is determined along the profile. The average value of the 5 measurements forms the average film thickness. The average film thickness along the cross section profile is determined using video light microscopy.

In an advantageous embodiment, the material of the water-soluble and/or water-dispersible film sachets of the portions according to the invention consists entirely or partially of a thermoplast chosen from the group comprising polyvinyl alcohol (PVA), acetalated polyvinyl alcohol, polyvinylpyrrolidone, polyethylene oxide, gelatin, cellulose, starch and derivatives of the abovementioned substances and/or mixtures of the abovementioned polymers, with polyvinyl alcohol being particularly advantageous.

The polyvinyl alcohols described above are commercially available, for example under the trade name Mowiol® (Clariant) Polyvinyl alcohols which are particularly suitable for the purposes of the present embodiment according to the invention are, for example, Mowiol® 3-83, Mowiol® 4-88, Mowiol® 5-88, Mowiol® 8-88 and Clariant L648.

Further polyvinyl alcohols suitable as material for the film sachet are ELVANOL® 51-05, 52-22, 50-42, 85-82, 75-15, T-25, T-66, 90-50 (trademark of Du Pont), ALCOTEX® 72.5, 78, B72, F80/40, F88/4, F88/26, F88/40, F88/47 (trademark of Harlow Chemical Co.), Gohsenol® NK-05, A-300, AH-22, C-500, GH-20, GL-03, GM-14L, KA-20, KA-500, KH-20, KP-06, N-300, NH-26, NM11Q, KZ-06 (trademark of Nippon Gohsei K.K.).

In a further advantageous embodiment, the film sachet material additionally has polymers chosen from the group comprising acrylic acid-containing polymers, polyacrylamides, oxazoline polymers, polystyrene sulfonates, polyurethanes, polyesters, polyethers and/or mixtures of the above polymers. It is advantageous if the coating material of the portion according to the invention constitutes a partially acetalated polyvinyl alcohol with a degree of hydrolysis of from 70 to 100 mol %, preferably 80 to 96 mol %, particularly advantageously 82 to 94 mol % and in particular 85 to 89 mol %. It is further advantageous that the water-soluble thermoplast used comprises a polyvinyl acetate whose average molecular weight is in the range from 10 000 to 100 000 gmol$^{-1}$, preferably from 11 000 to 90 000 gmol$^{-1}$, particularly advantageously from 12 000 to 80 000 gmol$^{-1}$, in particular from 13 000 to 70 000 gmol$^{-1}$ and specifically from 20 000 to 40 000 gmol$^{-1}$. The average molecular weights were determined by means of gel permeation chromatography. Surprisingly, it has been found that the dissolution rate can be considerably improved through particular selection of the molecular weight.

In a further embodiment, the coating material comprises said thermoplasts in amounts of at least 50% by weight, preferably of at least 70% by weight, particularly advantageously of at least 80% by weight and in particular of at least 90% by weight, in each case based on the weight of the overall coating material.

In a further advantageous embodiment of the present invention, the portions according to the invention have an internal volume of from 5 to 500 cm$^3$, preferably from 10 to 200 cm$^3$, particularly advantageously from 20 to 100 cm$^3$ and in particular from 30 to 70 cm$^3$. In the field of hair-treatment compositions in particular, portion sizes with an internal volume of from 30 to 70 cm$^3$ have proven particularly suitable since, on the one hand, they are easy for the end consumer to handle and, on the other hand, due to the limited internal volume, no problems as regards damage to the film sachet caused by the gravitational force of the cosmetic preparation arise.

The internal volume of the portion is the space in the portion which is able to accommodate the cosmetic preparation.

In a further embodiment of the present invention, the film sachet dissolves in water at 20° C. in less than 5 minutes, preferably less than 4 minutes and further advantageously less than 3 minutes and in particular between 2 and 0.5 minutes in water. The dissolution rate was determined by adding 0.07 g of coating material to a beaker containing 7 ml of water. During the dissolution phase, the water was stirred using a magnetic stirrer (60 rpm). The dissolution rate was determined by means of optical methods, starting from the point when the coating material was added to the stirred aqueous solution until complete dissolution (opacity measurement).

Individual doses are perceived by the consumer as being easy. The consumer takes the product in question, doses it and needs to think nothing more about measuring out suitable amounts. However, there may be situations where these supply forms are critical since adaptation of the dosage depending on the situation is no longer possible and thus, for example, one dosage unit is too little, but two units is too much. This problem can be solved by providing multichamber film sachets. The present embodiment according to the invention thus further provides a multichamber film sachet consisting of at least one portion according to the invention.

In a further advantageous embodiment, the multichamber film sachet consists of two or multicomponent individual portions which are joined together via ribs. Ribs here may also be common sealed areas of two adjacent portions.

In a further advantageous embodiment, the multichamber film sachets are such that they have two or three individual portions connected together which advantageously in each case have different cosmetic preparations. A multichamber system for the purposes of the present embodiment according to the invention can thus also be a system, for example, of two dye components (developer and coupler) which are located separately from one another in a multichamber film sachet. Advantageously, the multichamber film sachets according to the invention have two or more compartments in which preferably different cosmetic preparations, in particular hair colorant components, are located. Such multichamber film sachets further simplify dosing for the consumer since, in such a case, only a single packaging unit has to be dissolved in the corresponding use solution.

Cosmetic Preparations

The consistency of the cosmetic preparation which is surrounded by the water-soluble and/or water-dispersible coating is not subject to any particular requirements. Advantageously, the cosmetic preparations are in the form of powders, pastes, emulsions or gels.

The portions according to the invention have proven to be particularly advantageous in the field of hair-treatment compositions. In an advantageous embodiment, the cosmetic preparations are therefore hair-treatment compositions, in particular bleaching or hair colorants.

The water content of the cosmetic preparation is a critical value and should therefore preferably be below 20% by weight, preferably below 12% by weight, particularly advantageously below 8% by weight, further advantageously below 4% by weight, in particular below 2% by weight, in each case based on the total cosmetic preparation.

Bleaching Compositions:

In an advantageous embodiment, the portions according to the invention comprise one or more bleaching compositions as cosmetic preparation.

The principles of bleaching processes are known to the person skilled in the art and described comprehensively in relevant monographs, e.g. by K. Schrader, Grundlagen und Rezepturen der Kosmetika [Fundamentals and formulations of cosmetics], 2nd edition, 1989, Dr. Alfred Hüthig Verlag, Heidelberg, or W. Umbach (Ed.), Kosmetik [Cosmetics], 2nd edition, 1995, Georg Thieme Verlag, Stuttgart, N.Y.

For bleaching human hair—particularly for strand application—solid or paste-like preparations containing solid oxidizing agents are usually mixed directly prior to use with a dilute hydrogen peroxide solution. This mixture is then applied to the hair and rinsed out again after a certain contact time.

The specified preparations which are usually mixed prior to use with a hydrogen peroxide solution are termed below as "bleaching compositions". All of the amounts listed refer, unless stated otherwise, exclusively to these preparations and are given in percentages by weight, based on the preparation.

Bleaching compositions usually comprise a solid peroxo compound. The choice of this peroxo compound is in principle not subject to limitations; customary peroxo compounds known to the person skilled in the art are, for example, ammonium peroxydisulfate, potassium peroxydisulfate, sodium peroxydisulfate, ammonium persulfate, potassium persulfate, sodium persulfate, potassium peroxydiphosphate, percarbonates, such as magnesium percarbonate, peroxides, such as barium peroxide, and perborates, urea peroxide and melamine peroxide. Among these peroxo compounds, which can also be used in combination, the inorganic compounds are advantageous according to the invention. The peroxydisulfates, in particular combinations of at least two peroxydisulfates, are particularly advantageous.

The peroxo compounds are present in the bleaching compositions advantageously in amounts of 20–80% by weight, in particular in amounts of 40–70% by weight, in each case based on the total bleaching composition.

The bleaching compositions advantageously comprise an alkalizing agent which serves to establish the alkaline pH of the application mixture. Use may be made of the customary alkalizing agents likewise known to the person skilled in the art for bleaching compositions, such as ammonium, alkali metal and alkaline earth metal hydroxides, carbonates, carbamates, hydrogencarbonates, hydroxycarbonates, silicates, in particular metasilicates, and also alkali metal phosphates. In an advantageous embodiment, the bleaching compositions comprise at least two different alkalizing agents. Here, mixtures of, for example, a metasilicate and a hydroxycarbonate may be advantageous.

The bleaching compositions comprise alkalizing agents advantageously in amounts of 10–30% by weight, in particular 15–25% by weight.

In addition, bleaching compositions can comprise amines and/or diamines, for example monoethanolamine, triethanolamine, and 2-amino-2-methyl-1-propanol.

Further amines are ethoxylated coconut amines and derivatives of soya amine, in particular PEG-3 cocamine and dihydroxyethyl soya amine dioleate.

In addition, it has proven advantageous if the bleaching compositions comprise nonionogenic interface-active substances. Here, those interface-active substances which have an HLB value of 5.0 and greater are advantageous. For the definition of the HLB value, reference is made expressly to the details in Hugo Janistyn, Handbuch der Kosmetika und Riechstoffe [Handbook of cosmetics and fragrances], volume III: Die Körperpflegemittel [Bodycare compositions], 2nd edition, Dr. Alfred Hüthig Verlag Heidelberg, 1973, pages 68–78 and Hugo Janistyn, Taschenbuch der modernen Parfümerie und Kosmetik [Pocket book of modern perfumery and cosmetics], 4th edition, Wissenschaftliche Verlagsgesellschaft m.b.H. Stuttgart, 1974, pages 466–474, and the original works cited therein.

Particularly advantageous nonionogenic surface-active substances here are, due to simple processability, substances which are commercially available in pure form as solids or liquids. The definition of purity refers in this connection not to chemically pure compounds. Instead, particularly when the products are natural-based products, it is possible to use mixtures of different homologs, for example with different alkyl chain lengths, as are obtained with products based on natural fats and oils. In the case of alkoxylated products too, mixtures of different degrees of alkoxylation are usually present. The term purity refers in this connection rather to the fact that the chosen substances should be free from solvents, extenders and other accompanying substances.

Advantageous nonionogenic interface-active substances are
- alkoxylated fatty alcohols having 8 to 22, in particular 10 to 16, carbon atoms in the fatty alkyl group and 1 to 30, in particular 1 to 15, ethylene oxide and/or propylene oxide units. Preferred fatty alkyl groups are, for example, lauryl, myristyl, cetyl, but also stearyl, isostearyl and oleyl groups. Particularly preferred compounds of this class are, for example, lauryl alcohol having 2 to 4 ethylene oxide units, oleyl and cetyl alcohol having in each case 5 to 10 ethylene oxide units, cetyl and stearyl alcohol, and mixtures thereof having 10 to 30 ethylene oxide units, and the commercial product Aethoxal®B (Henkel), a lauryl alcohol having in each case 5 ethylene oxide and propylene oxide units. Besides the customary alkoxylated fatty alcohols, so-called "terminally capped" compounds can also be used according to the invention. In these compounds, the alkoxy group has no OH group at the end, but is "capped" in the form of an ether, in particular a $C_1$–$C_4$-alkyl ether. One example of such a compound is the commercial product Dehypon®LT 054, a $C_{12-18}$-fatty alcohol+4.5 ethylene oxide butyl ether.
- alkoxylated fatty acids having 8 to 22, in particular 10 to 16, carbon atoms in the fatty acid group and 1 to 30, in particular 1 to 15, ethylene oxide and/or propylene oxide units. Preferred fatty acids are, for example, lauric acid, myristic acid, palmitic acid, stearic acid, isostearic acid and oleic acid.
- alkoxylated, preferably propoxylated and in particular ethoxylated, mono-, di- and triglycerides. Examples of preferred compounds are glycerol monolaurate+20 ethylene oxide and glycerol monostearate+20 ethylene oxide.
- polyglycerol esters and alkoxylated polyglycerol esters. Preferred compounds of this class are, for example, poly(3)glycerol diisostearate (commercial product: Lameform®TGI (Henkel)) and poly(2)glycerol polyhydroxystearate (commercial product: Dehymuls®PGPH (Henkel).
- sorbitan fatty acid esters and alkoxylated sorbitan fatty acid esters, such as, for example, sorbitan monolaurate and sorbitan monolaurate+20 ethylene oxide (EO).
- alkylphenols and alkylphenol alkoxides having 6 to 21, in particular 6 to 15, carbon atoms in the alkyl chain and 0 to 30 ethylene oxide and/or propylene oxide units. Preferred representatives of this class are, for example, nonylphenol+4 EO, nonylphenol+9 EO, octylphenol+3 EO and octylphenol+8 EO.

Particularly preferred classes of nonionogenic interface-active substances are the alkoxylated fatty alcohols, the alkoxylated fatty acids, and the alkylphenols and alkylphenol alkoxylates.

Compositions which have proven particularly advantageous are those which comprise nonionogenic interface-active substances in amounts of 0.5–10% by weight.

In addition, the bleaching compositions can comprise all active ingredients, additives and auxiliaries known in such preparations. In many cases, the colorants comprise at least one surfactant, with both anionic and also zwitterionic, ampholytic and cationic surfactants being suitable in principle. In many cases, however, it has proven to be advantageous to choose the surfactants from anionic, cationic or nonionic surfactants. Anionic surfactants may be very particularly preferred here.

Preferred anionic surfactants are alkyl sulfates, ether carboxylic acid salts having 10 to 18 carbon atoms in the alkyl group and up to 12 glycol ether groups in the molecule, such as $C_{12}H_{25}$—$(C_2H_4O)_6$—$CH_2$—COONa, and in particular salts of saturated and specifically unsaturated $C_8$–$C_{22}$-carboxylic acids, such as oleic acid, stearic acid, isostearic acid and palmitic acid.

These anionic surfactants should preferably be present in solid form, in particular powder form. Very particular preference here is given to soaps which are solid at room temperature, in particular sodium stearate. These are preferably present in amounts of from 5 to 20% by weight, in particular 10 to 15% by weight.

Suitable nonionic surfactants are, in particular, $C_8$–$C_{22}$-alkyl mono- and oligoglycosides and ethoxylated analogs thereof. In particular, the nonethoxylated compounds which are additionally commercially available in powder form have proven to be particularly suitable.

Examples of the cationic surfactants which can be used in the hair-treatment compositions are in particular quaternary ammonium compounds. Preference is given to ammonium halides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Further cationic surfactants which can be used according to the invention are the quaternized protein hydrolyzates.

Alkylamidoamines, in particular fatty acid amidoamines, such as the stearylamidopropyldimethylamine obtainable under the name Tego Amid®S 18 are characterized specifically by their good biodegradability as well as a good conditioning effect.

Likewise of very good biodegradability are quaternary ester compounds, so-called ester quats, such as the distearoylethylhydroxyethylammonium methosulfate obtainable in a mixture with cetearyl alcohol under the name Dehyquart®F 75.

The compounds with alkyl groups used as surfactants may in each case be uniform substances. However, it is usually preferred to prepare these substances starting from natural vegetable or animal raw materials, thus leading to mixtures of substances with varying alkyl chain lengths which depend on the particular raw material.

Further active ingredients, auxiliaries and additives are, for example, nonionic polymers, such as, for example, vinylpyrrolidone/vinyl acrylate copolymers, polyvinylpyrrolidone and vinylpyrrolidone/vinyl acetate copolymers and polysiloxanes, cationic polymers, such as quaternized cellulose ethers and other compounds which are stable as solid and commercially available, zwitterionic and amphoteric polymers which are stable as solids and are preferably obtainable as commercial products, anionic polymers, such as, for example, polyacrylic acids, crosslinked polyacrylic acids and vinyl acetate/crotonic acid copolymers provided these are stable as solids and are preferably available commercially, thickeners, such as agar agar, guar gum, alginates, xanthan gum, gum arabic, karaya gum, carob seed flour, linseed gums, dextrans, cellulose derivatives, e.g. methylcellulose, hydroxyalkylcellulose and carboxymethylcellulose, starch fractions and derivatives, such as amylose, amylopectin and dextrins, clays, such as, for example, bentonite or completely synthetic hydrocolloids, such as, for example, polyvinyl alcohol, structurants, such as glucose, maleic acid and lactic acid, hair-conditioning compounds, such as phospholipids, for example soya lecithin, egg lecithin and cephalins, and silicone oils protein hydrolyzates, in particular elastin, collagen, keratin, milk protein, soya protein and wheat protein hydrolyzates, their condensation products with fatty acids, and quaternized protein hydrolyzates, perfume oils, dimethyl isosorbide and cyclodextrins, dyes for coloring the preparations, active ingredients, such as panthenol, pantothenic acid, allantoin, pyrrolidonecarboxylic acids and salts thereof, cholesterol, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration auxiliaries, such as carbonates, hydrogencarbonates, guanidines, ureas, and primary, secondary and tertiary phosphates.

The person skilled in the art will choose these further substances according to the desired properties of the compositions.

The bleaching compositions can be prepared by the customary methods known to the person skilled in the art.

One method consists in initially introducing the inorganic components present as a solid, optionally after mixing, e.g. in a Drais mixer, and spraying them with the interface-active composition. This is preferably carried out at room temperature, i.e. at temperatures below about 30° C.; only if the chosen dust-binding components are not in the form of a liquid at these temperatures will elevated temperatures be used.

A further preparation method for the bleaching compositions is the grinding of all components in a ball mill, a ring-roller mill or, in particular, a spindle mill.

Finally, it is possible to prepare the pulverulent bleaching compositions by mixing all of the components and subsequently treating them, preferably at elevated temperatures, in a fluidized bed.

The bleaching compositions can be in liquid, gel-like, paste or powder form.

Preferred cosmetic preparations are bleaching compositions in powder form. It has been found that particularly bleaching powders which have an average particle size below 250 µm, preferably between 50 and 150 µm, are suitable for the portions according to the invention.

The particle sizes were measured using a Coulter counter. The portions according to the invention which comprise bleaching composition as cosmetic preparation are usually mixed directly prior to application with a hydrogen peroxide solution and dissolved in this.

The concentration of this hydrogen peroxide solution is on the one hand determined by the legal stipulations and on the other hand by the desired effect; as a rule 6 to 12 percent strength solutions in water are used. The quantitative ratios of bleaching composition and hydrogen peroxide solution here are usually in the range 1:1 to 1:2, with an excess of hydrogen peroxide solution being chosen particularly if a none too marked bleaching effect is desired.

Hair Colorants:

In a further embodiment, the portions according to the invention comprise hair colorants as cosmetic preparation. The hair colorants are preferably chosen from the group of temporary colorants, semipermanent colorants and permanent hair colorants, in particular chosen from the group of colorants with reactive carbonyl compounds (oxo colorants), oxidation colorants, specifically chosen from developer components or coupler components or the components A or B of an oxo colorant.

Temporary hair colorants are suitable for bringing about temporary colorations on keratin fibers.

For temporary colorations, use is usually made of colorants or tints which comprise so-called direct dyes as coloring component. These are dye molecules which attach directly to the hair and require no oxidative process for developing the color. These dyes include, for example, henna, which has been known since antiquity for coloring bodies and hair. These colorations are generally significantly more sensitive to shampooing than oxidative colorations, meaning that an often undesired nuance shift or even a visible "decoloring" then takes place very much more quickly.

Semipermanent hair colorants are characterized by more strongly marked and more permanent color nuances.

They are resistant to up to 5–6 hair washes. The dyes used must, accordingly, have a high affinity to the keratin and penetrate relatively deeply into the surface of the hair fiber. The most important representatives of this group of dyes are 2-nitro-1,4-phenylenediamine and nitroaniline derivatives. The likewise used so-called arianor dyes are azo or quinoneimine dyes with quaternary ammonium groups. The presence of glycol ethers, cyclohexanol or benzyl alcohol in the solvent system promotes the keratin affinity of the dyes.

Permanent hair colorants are widespread. The permanent hair coloration is largely resistant to the effects of light and weathering and to all customary hair-treatment methods and only needs to be renewed approximately monthly, due to hair regrowth.

The definitions of hair colorants are given in Römpp Lexikon Chemie [Römpp's chemistry lexicon], version 2.0, Stuttgart/New York: Georg Thieme Verlag 1999.

In a particularly preferred embodiment, the portions according to the invention comprise oxidation colorants. Oxidation colorants are usually used for permanent, intense colorations.

Such colorants usually comprise oxidation dye precursors, so-called developer components and coupler components. Under the influence of oxidizing agents or of atmospheric oxygen, the developer components form, with one another or with coupling with one or more coupler components, the actual dyes. For colorations with a natural effect, use is usually made of a mixture of a relatively large number of oxidation dye precursors; in many cases, direct dyes are also used for the nuancing.

The coloring preparation comprising the developer and coupler components and the oxidizing agent—in most cases a hydrogen peroxide preparation—are usually mixed together shortly prior to application. In a preferred embodiment of the present embodiment according to the invention, at least one coloring preparation or one oxidizing agent preparation is located in a portion according to the invention. Preferably, the portions are present separately alongside one another, i.e. as portion comprising colorant preparation, preferably coloring preparation comprising developer and/or coupler components, and as portion comprising oxidizing agent.

The oxidation colorant is particularly preferably present in a multichamber container in which there is, in at least one chamber, a coloring preparation, preferably coloring preparation comprising developer and/or coupler components, and, in at least one other chamber of the container, at least one oxidizing agent preparation.

Developer Component:

Suitable developer components are, for example, p-phenylenediamine derivatives or one of its physiologically compatible salts of the formula (E1)

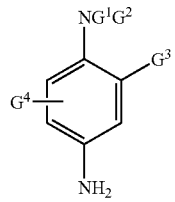

(E1)

where
$G^1$ is a hydrogen atom, a $C_1$–$C_4$-alkyl radical, a $C_1$–$C_3$-monohydroxyalkyl radical, a $C_2$–$C_6$-polyhydroxyalkyl radical, a ($C_1$–$C_4$)-alkoxy-($C_1$–$C_4$)-alkyl radical, a 4-aminophenyl radical or a $C_1$–$C_4$-alkyl radical which is substituted by a nitrogen-containing group, a phenyl radical or a 4-aminophenyl radical;
$G^2$ is a hydrogen atom, a $C_1$–$C_4$-alkyl radical, a $C_1$–$C_3$-monohydroxyalkyl radical, a $C_2$–$C_6$-polyhydroxyalkyl radical, a ($C_1$–$C_4$)-alkoxy-($C_1$–$C_4$)-alkyl radical or a $C_1$–$C_4$-alkyl radical which is substituted by a nitrogen-containing group;
$G^3$ is a hydrogen atom, a halogen atom, such as a chlorine, bromine, iodine or fluorine atom, a $C_1$–$C_4$-alkyl radical, a $C_1$–$C_4$-monohydroxyalkyl radical, a $C_2$–$C_6$-polyhydroxyalkyl radical, a $C_1$–$C_4$-hydroxyalkoxy radical, a $C_1$–$C_4$-acetylaminoalkoxy radical, a $C_1$–$C_4$-mesylaminoalkoxy radical or a $C_1$–$C_4$-carbamoylaminoalkoxy radical;
$G^4$ is a hydrogen atom, a halogen atom or a $C_1$–$C_4$-alkyl radical or
if $G^3$ and $G^4$ are in the ortho position relative to one another, they can together form a bridging $\alpha,\omega$-alkylenedioxo group, such as, for example, an ethylenedioxy group.

Examples of the $C_1$–$C_3$-alkyl radicals specified as substituents in the compounds according to the invention are the groups methyl, ethyl, propyl and isopropyl. Ethyl and methyl are generally preferred alkyl radicals. Advantageous $C_1$–$C_4$-alkoxy radicals are, for example, a methoxy or an ethoxy group. In addition, preferred examples of a $C_1$–$C_4$-monohydroxyalkyl group which may be mentioned are a hydroxymethyl group, a 2-hydroxyethyl group, a 3-hydroxypropyl group or a 4-hydroxybutyl group. A 2-hydroxyethyl group is particularly preferred. A particularly preferred $C_2$–$C_4$-polyhydroxyalkyl group is the 1,2-dihydroxyethyl group. Examples of halogen atoms according to the invention are F, Cl or Br atoms; Cl atoms are very particularly preferred. According to the invention, the other terms used are derived from the definitions given here. Examples of nitrogen-containing groups of the formula (E1) are, in particular, the amino groups, $C_1$–$C_4$-monoalkylamino groups, $C_1$–$C_4$-dialkylamino groups, $C_1$–$C_4$-trialkylammonium groups, $C_1$–$C_4$-monohydroxyalkylamino groups, imidazolinium and ammonium.

Particularly preferred p-phenylenediamines of the formula (E1) are chosen from p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis($\beta$-hydroxyethyl)-p-phenylenediamine, 4-N,N-bis($\beta$-hydroxyethyl)amino-2-methylaniline, 4-N,N-bis($\beta$-hydroxyethyl)amino-2-chloroaniline, 2-($\beta$-hydroxyethyl)-p-phenylenediamine, 2-($\alpha,\beta$-dihydroxyethyl)-p-phenylenediamine, 2-fluoro-p-phenylenediamine, 2-isopropyl-p-phenylenediamine, N-($\beta$-hydroxypropyl)-p-phenylenediamine, 2-hydroxymethyl-p-phenylenediamine, N,N-dimethyl-3-methyl-p-phenylenediamine, N,N-(ethyl,$\beta$-hydroxyethyl)-p-phenylenediamine, N-($\beta,\gamma$-dihydroxypropyl)-p-phenylenediamine, N-(4-aminophenyl)-p-phenylenediamine, N-phenyl-p-phenylenediamine, 2-($\beta$-hydroxyethyloxy)-p-phenylenediamine, 2-($\beta$-acetylaminoethyloxy)-p-phenylenediamine, N-($\beta$-methoxyethyl)-p-phenylenediamine and 5,8-diaminobenzo-1,4-dioxane, and their physiologically compatible salts.

According to the invention, very particularly preferred p-phenylenediamine derivatives of the formula (E1) are p-phenylenediamine, p-tolylenediamine, 2-($\beta$-hydroxyethyl)-p-phenylenediamine, 2-($\alpha,\beta$-dihydroxyethyl)-p-phenylenediamine and N,N-bis($\beta$-hydroxyethyl)-p-phenylenediamine.

It may also be advantageous to use, as developer component, compounds which contain at least two aromatic nuclei which are substituted by amino and/or hydroxyl groups.

Among the binuclear developer components which can be used in the coloring compositions according to the embodiment of the invention, mention may be made in particular of the compounds which conform to the following formula (E2), and their physiologically compatible salts:

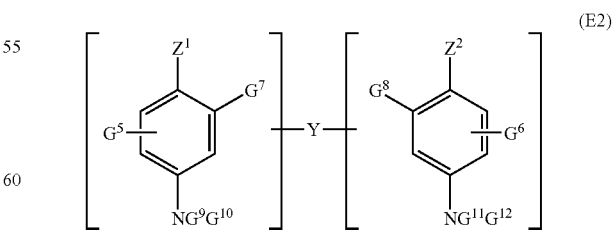

(E2)

where:
$Z^1$ and $Z^2$, independently of one another, are a hydroxyl or $NH_2$ radical which is optionally substituted by a $C_1$–$C_4$- alkyl radical, by a $C_1$–$C_4$-hydroxyalkyl radical and/or by a bridge Y or which is optionally part of a bridging ring system, the bridge Y is an alkylene group having 1 to 14 carbon atoms, such as, for example, a linear or branched alkylene chain or an alkylene ring which can be terminated or interrupted by one or more nitrogen-containing groups and/or one or more heteroatoms, such as oxygen, sulfur or nitrogen atoms, and may possibly be substituted by one or more hydroxyl or $C_1$–$C_8$-alkoxy radicals, or a direct bond, $G^5$ and $G^6$, independently of one another, are a hydrogen or halogen atom, a $C_1$–$C_4$-alkyl radical, a $C_1$–$C_4$-monohydroxyalkyl radical, a $C_2$–$C_6$-polyhydroxyalkyl radical, a $C_1$–$C_4$-aminoalkyl radical or a direct bond to the bridge Y, $G^7$, $G^8$, $G^9$, $G^{10}$, $G^{11}$ and $G^{12}$, independently of one another, are a hydrogen atom, a direct bond to the bridge Y or a $C_1$–$C_4$-alkyl radical, with the provisos that the compounds of the formula (E2) contain only one bridge Y per molecule and the compounds of the formula (E2) contain at least one amino group which carries at least one hydrogen atom.

According to the invention, the substituents used in formula (E2) are defined analogously to the above statements.

Preferred binuclear developer components of the formula (E2) are in particular: N,N'-bis(β-hydroxyethyl)-N,N'-bis(4-aminophenyl)-1,3-diaminopropan-2-ol, N,N'-bis(β-hydroxyethyl)-N,N'-bis(4-aminophenyl)ethylenediamine, N,N'-bis(4-amino-phenyl)tetramethylenediamine, N,N'-bis (β-hydroxyethyl)-N,N'-bis(4-aminophenyl)tetramethylenediamine, N,N'-bis(4-methyl-aminophenyl)tetramethylenediamine, N,N'-diethyl-N,N'-bis(4-amino-3-methylphenyl) ethylenediamine, bis(2-hydroxy-5-aminophenyl)methane, N,N'-bis(4-aminophenyl)-1,4-diazacycloheptane, N,N'-bis (2-hydroxy-5-aminobenzyl)piperazine, N-(4-aminophenyl)-p-phenylenediamine and 1,10-bis(2,5-diaminophenyl)-1,4,7,10-tetraoxadecane and their physiologically compatible salts.

Very particularly preferred binuclear developer components of the formula (E2) are N,N'-bis(β-hydroxyethyl)-N,N'-bis(4-aminophenyl)-1,3-diaminopropan-2-ol, bis(2-hydroxy-5-aminophenyl)methane, N,N'-bis(4-aminophenyl)-1,4-diazacycloheptane and 1,10-bis(2,5-diaminophenyl)-1,4,7,10-tetraoxadecane or one of their physiologically compatible salts.

In addition, it may be advantageous to use a p-aminophenol derivative or one of its physiologically compatible salts as developer component. Particular preference is given to p-aminophenol derivatives of the formula (E3)

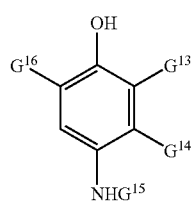

(E3)

where:

$G^{13}$ is a hydrogen atom, a halogen atom, a $C_1$–$C_4$-alkyl radical, a $C_1$–$C_4$-monohydroxyalkyl radical, a $C_2$–$C_6$-polyhydroxyalkyl radical, a ($C_1$–$C_4$)-alkoxy-($C_1$–$C_4$)-alkyl radical, a $C_1$–$C_4$-aminoalkyl radical, a hydroxy-($C_1$–$C_4$)-alkylamino radical, a $C_1$–$C_4$-hydroxyalkoxy radical, a $C_1$–$C_4$-hydroxyalkyl-($C_3$–$C_4$)-aminoalkyl radical or a (di-$C_1$–$C_4$-alkylamino)-($C_1$–$C_4$)-alkyl radical, and $G^{14}$ is a hydrogen or halogen atom, a $C_1$–$C_4$-alkyl radical, a $C_1$–$C_4$-monohydroxyalkyl radical, a $C_2$–$C_6$-polyhydroxyalkyl radical, a ($C_1$–$C_4$)-alkoxy-($C_1$–$C_4$)-alkyl radical, a $C_1$–$C_4$-aminoalkyl radical or a $C_1$–$C_4$-cyanoalkyl radical, $G^{15}$ is is hydrogen, a $C_1$–$C_4$-alkyl radical, a $C_1$–$C_4$-monohydroxyalkyl radical, a $C_2$–$C_6$-polyhydroxyalkyl radical, a phenyl radical or a benzyl radical, and $G^{16}$ is hydrogen or a halogen atom.

According to the invention, the substituents used in formula (E3) are defined analogously to the above statements.

Preferred p-aminophenols of the formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol and their physiologically compatible salts.

Very particularly preferred compounds of the formula (E3) are p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

In addition, the developer component can be chosen from o-aminophenol and its derivatives, such as, for example, 2-amino-4-methylphenol, 2-amino-5-methylphenol or 2-amino-4-chlorophenol.

In addition, the developer component can be chosen from heterocyclic developer components, such as, for example, the pyridine, pyrimidine, pyrazole, pyrazolopyrimidine derivatives and their physiologically compatible salts.

Preferred pyridine derivatives are, in particular, the compounds which are described in the patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine.

Preferred pyrimidine derivatives are, in particular, the compounds which are described in the German patent DE 2 359 399, the Japanese laid-open specification JP 02019576 A2 or in the laid-open specification WO 96/15765, such as 2,4,5,6-tetraamino-pyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are, in particular, the compounds which are described in the patents DE 3 843 892, DE 4 133 957 and patent applications WO 94/08969, WO 94/08970, EP-740 931 and DE 195 43 988, such as 4,5-diamino-1-methylpyrazole, 4,5-diamino-1-(β-hydroxyethyl)pyrazole, 3,4-diaminopyrazole, 4,5-diamino-1-(4-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3- hydroxymethyl-1-methylpyrazole, 4,5-diamino-3-hydroxymethyl-1-isopropylpyrazole, 4,5-diamino-3-methyl-1-isopropylpyrazole, 4-amino-5-(☐-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxy-ethyl)amino-1-methylpyrazole.

Preferred pyrazolopyrimidine derivatives are, in particular, the derivatives of pyrazolo[1,5-a]pyrimidine of the following formula (E4) and its tautomeric forms if a tautomeric equilibrium exists:

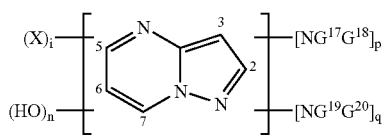

where:

$G^{17}$, $G^{18}$, $G^{19}$ and $G^{20}$, independently of each other, are a hydrogen atom, a $C_1$–$C_4$-alkyl radical, an aryl radical., a $C_1$–$C_4$-hydroxyalkyl radical, a $C_2$–$C_4$-polyhydroxyalkyl radical, a $(C_1$–$C_4)$-alkoxy-$(C_1$–$C_4)$ -alkyl radical, a $C_1$–$C_4$-aminoalkyl radical, which may be optionally protected by an acetyl ureido or a sulfonyl radical, a $(C_1$–$C_4)$-alkylamino-$(C_1$–$C_4)$-alkyl radical, a di[$(C_1$–$C_4)$-alkyl]-$(C_1$–$C_4)$-aminoalkyl radical, where the dialkyl radicals optionally form a carbon cycle or a heterocycle with 5 or 6 chain members, a $C_1$–$C_4$-hydroxyalkyl radical or a di $(C_1$–$C_4)$-[hydroxyalkyl]-$(C_1$–$C_4)$-aminoalkyl radical, the X radicals, independently of each other, are a hydrogen atom, a $C_1$–$C_4$-alkyl radical, an aryl radical, a $C_1$–$C_4$-hydroxyalkyl radical, a $C_2$–$C_4$-polyhydroxyalkyl radical, a $C_1$–$C_4$-aminoalkyl radical, a $(C_1$–$C_4)$-alkylamino-$(C_1$–$C_4)$-alkyl radical, a di [$(C_1$–$C_4)$alkyl]-$(C_1$–$C_4)$-aminoalkyl radical, where the dialkyl radicals optionally form a carbon cycle or a heterocycle with 5 or 6 chain members, a $C_1$–$C_4$-hydroxyalkyl or a di$(C_1$–$C_4$-hydroxyalkyl) aminoalkyl radical, an amino radical, a $C_1$–$C_4$-alkyl- or di$(C_1$–$C_4$-hydroxyalkyl)amino radical, a halogen atom, a carboxylic acid group or a sulfonic acid group, i has the value 0, 1, 2 or 3, p has the value 0 or 1, q has the value 0 or 1 and n has the value 0 or 1, with the proviso that the sum of p+q is not 0, if p+q is 2, n has the value 0, and the groups $NG^{17}G^{18}$ and $NG^{19}G^{20}$ occupy the positions (2,3); (5,6); (6,7); (3,5) or (3,7);

if p+q is 1, n has the value 1, and the groups $NG^{17}G^{18}$ (or $NG^{19}G^{20}$) and the group OH occupy the positions (2,3); (5,6); (6,7); (3,5) or (3,7);

According to the invention, the substituents used in formula (E4) are defined analogously to the above statements.

If the pyrazolo[1,5-a]pyrimidine of the above formula (E4) contains a hydroxy group at one of positions 2, 5 or 7 of the ring system, a tautomeric equilibrium exists which is represented, for example, in the following scheme:

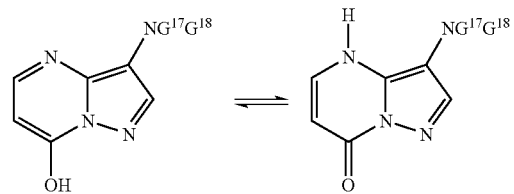

Among the pyrazolo[1,5-a]pyrimidines of the above formula (E4) mention may be made in particular of:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
3-amino-7-dimethylamino-2,5-dimethylpyrazolo-[1,5-a]pyrimidine;

and their physiologically compatible salts and their tautomeric forms if a tautomeric equilibrium is present.

The pyrazolo[1,5-a]pyrimidines of the above formula (E4) can be prepared as described in the literature by cyclization starting from an aminopyrazole or from hydrazine.

Coupler Components:

The portions according to the invention preferably comprise at least one coupler component. The coupler components used are generally m-phenylenediamine derivatives, naphthols, resorcinol and resorcinol derivatives, pyrazolones and m-aminophenol derivatives. Suitable coupler substances are, in particular, 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methylpyrazol-5-one, 2,4-dichloro-3-aminophenol, 1,3-bis(2,4-diaminophenoxy)-propane, 2-chlororesorcinol, 4-chlororesorcinol, 2-chloro-6-methyl-3-aminophenol, 2-amino-3-hydroxypyridine, 2-methylresorcinol, 5-methylresorcinol and 2-methyl-4-chloro-5-aminophenol.

Coupler components preferred according to the invention are
m-aminophenol and its derivatives, such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol and 2,4-dichloro-3-aminophenol,
o-aminophenol and derivatives thereof, m-diaminobenzene and derivatives thereof, such as, for example, 2,4-diaminophenoxyethanol, 1,3-bis (2,4-diaminophenoxy)propane, 1-methoxy-2-amino-4-(2-hydroxyethylamino)benzene, 1,3-bis(2,4-diaminophenyl) propane, 2,6-bis(2-hydroxyethylamino)-1-methylbenzene and 1-amino-3-bis(2-hydroxyethyl)aminobenzene, o-diaminobenzene and derivatives thereof, such as, for example, 3,4-diaminobenzoic acid and 2,3-diamino-1-methylbenzene, di- and trihydroxybenzene derivatives, such as, for example, resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene, pyridine derivatives, such as, for example, 2,6-di-hydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene, morpholine derivatives, such as, for example, 6-hydroxybenzomorpholine and 6-aminobenzomorpholine, quinoxaline derivatives, such as, for example, 6-methyl-1,2,3,4-tetrahydroquinoxaline, pyrazole derivatives, such as, for example, 1-phenyl-3-methylpyrazol-5-one, indole derivatives, such as, for example, 4-hydroxyindole, 6-hydroxyindole and 7-hydroxyindole, pyrimidine derivatives, such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, or methylenedioxybenzene derivatives, such as, for example, 1-hydroxy-3,4-methylenedioxybenzene, 1-amino-3,4-methylenedioxybenzene and 1-(2-hydroxyethyl)amino-3,4-methylenedioxybenzene.

Coupler components which are particularly preferred according to the invention are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

In a further preferred embodiment, the portions according to the invention comprise nature-analogous hair dye precursors. Dyeing with nature-analogous dyes has been given a lot of attention.

In this method, precursors of the natural hair dye melanine are applied to the hair; these then form nature-analogous dyes in the course of oxidative processes within the hair. Such a method with 5,6-dihydroxyindoline as dye precursor has been described in EP-B1-530 229. In the case of, in particular multiple, application of compositions comprising 5,6-dihydroxyindoline, it is possible to restore the natural hair color in people with gray hair. The coloration can take place here with atmospheric oxygen as the sole oxidizing agent, meaning that it is not necessary to have recourse to further oxidizing agents. In people with originally medium-blond to brown hair, the indoline can be used as the sole dye precursor. For use with people with originally red and, in particular, dark to black hair color, by contrast, satisfactory results can often only be achieved through the co-use of further dye components, in particular special oxidation dye precursors. The precursors of nature-analogous dyes used are preferably those indoles and indolines which have at least one hydroxy or amino group, preferably as substituent on the 6-membered ring. These groups can carry further substituents, e.g. in the form of an etherification or esterification of the hydroxy group or an alkylation of the amino group. In a second preferred embodiment, the colorants comprise at least one indole and/or indoline derivative.

Particularly suitable precursors of nature-analogous hair dyes are derivatives of 5,6-dihydroxyindoline of the formula (VIIa),

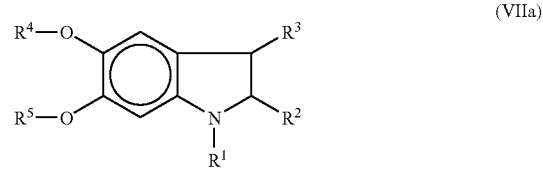

(VIIa)

in which, independently of one another, $R^1$ is hydrogen, a $C_1$–$C_4$-alkyl group or a $C_1$–$C_4$-hydroxyalkyl group, $R^2$ is hydrogen or a —COOH group, where the —COOH group can also be present as a salt with a physiologically compatible cation, $R^3$ is hydrogen or a $C_1$–$C_4$-alkyl group, $R^4$ is hydrogen, a $C_1$–$C_4$-alkyl group or a group —CO—$R^6$ in which $R^6$ is a $C_1$–$C_4$-alkyl group, and $R^5$ is one of the groups specified under $R^4$, and physiologically compatible salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, and 6-hydroxyindoline, 6-aminoindoline and 4-aminoindoline.

Within this group, particular emphasis is given to N-methyl-5,6-dihydroxyindoline, N-ethyl-5,6-dihydroxyindoline, N-propyl-5,6-dihydroxyindoline, N-butyl-5,6-dihydroxyindoline and in particular 5,6-dihydroxyindoline.

Exceptionally suitable precursors of nature-analogous hair dyes are also derivatives of 5,6-dihydroxyindole of the formula (VIIb),

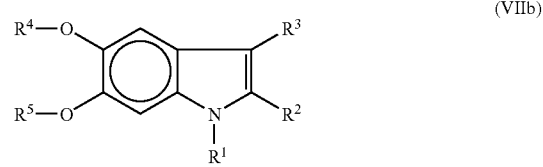

(VIIb)

in which, independently of one another, $R^1$ is hydrogen, a $C_1$–$C_4$-alkyl group or a $C_1$–$C_4$-hydroxyalkyl group, R² is hydrogen or a —COOH group, where the —COOH group can also be present as a salt with a physiologically compatible cation, R³ is hydrogen or a C₁–C₄-alkyl group, R⁴ is hydrogen, a C₁–C₄-alkyl group or a group —CO—R⁶ in which R⁶ is a C₁–C₄-alkyl group, and R⁵ is one of the groups specified under R⁴, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, emphasis is placed on N-methyl-5,6-dihydroxyindole, N-ethyl-5,6-dihydroxyindole, N-propyl-5,6-dihydroxyindole, N-butyl-5,6-dihydroxyindole and in particular 5,6-dihydroxyindole.

The indoline and indole derivatives can be used in the colorants used within the scope of the method according to the invention either as free bases or in the form of their physiologically compatible salts with inorganic or organic acids, e.g. hydrochlorides, sulfates and hydrobromides. The indole or indoline derivatives are present in these usually in amounts of 0.05–10% by weight, preferably 0.2–5% by weight.

In a further embodiment, it may be advantageous to use the indoline or indole derivative in hair colorants in combination with at least one amino acid or an oligopeptide. The amino acid is advantageously an α-amino acid; very particularly preferred α-amino acids are arginine, ornithine, lysine, serine and histidine, in particular arginine.

Direct Dyes:

In a further embodiment, the portions according to the invention additionally or individually comprise at least one direct dye. Direct dyes often serve to nuance the hair colors and are therefore advantageously added to permanent hair dyes, such as, for example, the abovementioned developer components, coupler components, nature-analogous hair dye precursors or to the components of oxo colorants.

Direct dyes are usually nitrophenylenediamines, nitroaminophenols, azo dyes, anthraquinones or indophenols. Preferred direct dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 12, Disperse Blue 3, HC Violet 1, Disperse Violet 1, Disperse Violet 4, Acid Violet 43, Disperse Black 9 and Acid Black 52, and also 1,4-diamino-2-nitrobenzene, 2-amino-4-nitrophenol, 1,4-bis(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureido-ethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

In addition, the compositions according to the invention can comprise a cationic direct dye. In this connection, particular preference is given to (a) cationic triphenylmethane dyes, such as, for example, Basic Blue 7, Basic Blue 26, Basic Violet 2 and Basic Violet 14, (b) aromatic systems which are substituted by a quaternary nitrogen group, such as, for example, Basic Yellow 57, Basic Red 76, Basic Blue 99, Basic Brown 16 and Basic Brown 17, and (c) direct dyes which contain a heterocycle which has at least one quaternary nitrogen atom, as are specified, for example, in EP-A2-998 908, to which reference is explicitly made at this point.

Preferred cationic direct dyes of group (c) are, in particular, the following compounds:

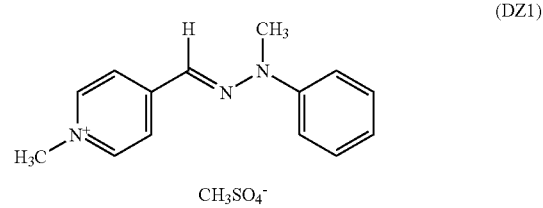
(DZ1)

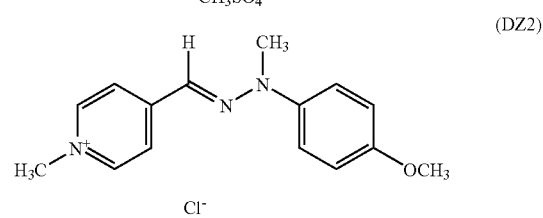
(DZ2)

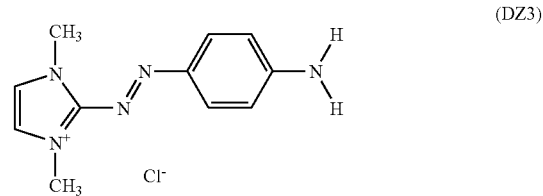
(DZ3)

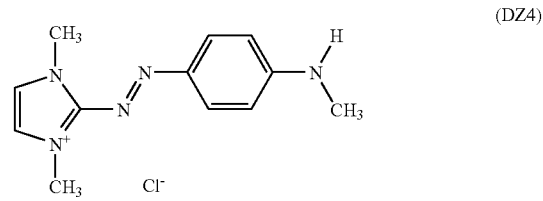
(DZ4)

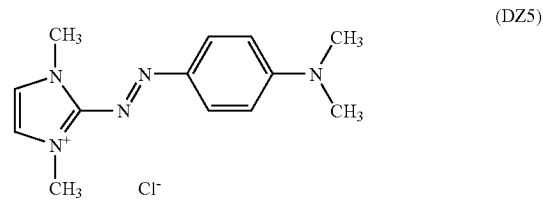
(DZ5)

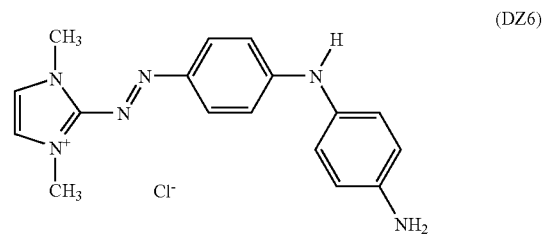
(DZ6)

-continued

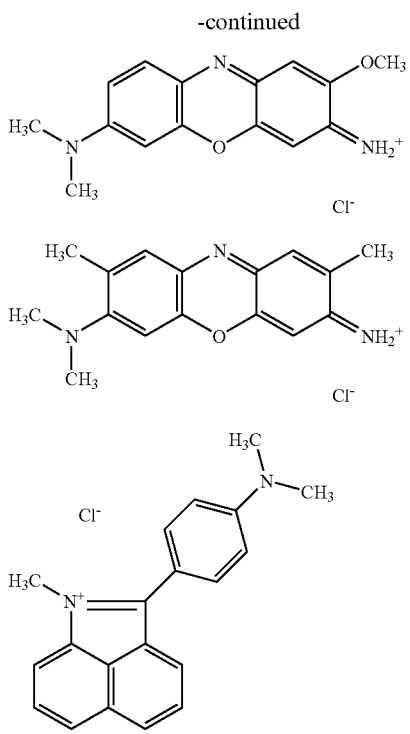

The compounds of the formulae (DZ1), (DZ3) and (DZ5) are very particularly preferred cationic direct dyes of group (c). The cationic direct dyes which are sold under the trade name Arianor® are advantageous direct dyes.

In a further embodiment, the portions according to the invention additionally comprise naturally occurring dyes, as are present, for example, in henna red, henna neutral, henna black, camomile blossom, sandalwood, black tea, buckthorn bark, sage, logwood, madder root, catechu, sedre and alkanna root.

Oxo Coloring:

In a particularly preferred embodiment, the portions according to the invention comprise components (component A or B) which are used for the oxo coloring.

Oxo colorants offer the possibility of coloring keratin-containing fibers by means of using a combination of component A) compounds which contain a reactive carbonyl group with component B): compounds chosen from (a) CH-acidic compounds, (b) compounds with a primary or secondary amino group or hydroxy group, chosen from primary or secondary aromatic amines, nitrogen-containing heterocyclic compounds and aromatic hydroxy compounds, (c) amino acids, (d) oligopeptides constructed from 2 to 9 amino acids.

The corresponding coloring method (called oxo coloring below) is described, for example, in the publications WO-A1-99/18916, WO-A1-00/38638, WO-A1-01/34106 and WO-A1-01/47483. Some of the resulting colorations have color fastnesses on the keratin-containing fibers which are comparable with those of oxidation coloring. The nuance spectrum which can be achieved with the gentle oxo coloring is very broad and the coloration obtained often has an acceptable brilliance and color depth. The abovementioned components A and B, referred to below as oxo dye precursors, are generally themselves not dyes, and are therefore, each taken by itself, unsuitable for coloring keratin-containing fibers on their own. In combination, they form dyes in a nonoxidative process. Among compounds of component B, however, it is also possible to use corresponding oxidation dye precursors of the developer type and/or coupler type with or without the use of an oxidizing agent. The method of oxo coloring can thus be directly combined with the oxidative coloring system.

In the course of the oxo coloring, reactive carbonyl compounds are used as component A, which forms the actual dye within the hair, in particular following reaction with a component B. Preferred reactive carbonyl compounds are aldehydes and ketones in which the reactive carbonyl group is present either as carbonyl group or derivatized or masked in such a way that the reactivity of the carbon atom of the derivatized carbonyl group toward the compounds of component B is always present. These derivatives are preferably addition compounds a) of amines and derivatives thereof with the formation of imines or oximes as addition compound
b) of alcohols with the formation of acetals or ketals as addition compound
c) of water with the formation of hydrates as addition compound (component A is derived in this case c) from an aldehyde ab) onto the carbon atom of the carbonyl group of the reactive carbonyl compound.

Component A is preferably chosen from compounds according to formula (Ox1),

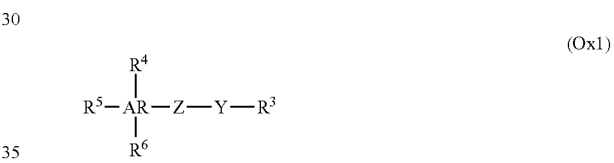

where

AR is benzene, naphthalene, pyridine, pyrimidine, pyrazine, pyridazine, carbazole, pyrrole, pyrazole, furan, thiophene, 1,2,3-triazine, 1,3,5-triazine, quinoline, isoquinoline, indole, indoline, indolizine, indane, imidazole, 1,2,4-triazole, 1,2,3-triazole, tetrazole, benzimidazole, 1,3-thiazole, benzothiazole, indazole, benzoxazole, quinoxaline, quinazoline, quinolizine, cinnoline, acridine, julolidine, acenaphthene, fluorene, biphenyl, diphenylmethane, benzophenone, diphenyl ether, azobenzene, chromone, coumarin, diphenylamine, stilbene, where the N-heteroaromatics can also be quaternized, $R^3$ is a hydrogen atom, a $C_1$–$C_6$-alkyl group, $C_2$–$C_6$-acyl group, $C_2$–$C_6$-alkenyl group, $C_1$–$C_4$-perfluoroalkyl group, an optionally substituted aryl group or heteroaryl group, $R^4$, $R^5$ and $R^6$, independently of one another, are a hydrogen atom, a halogen atom, a $C_1$–$C_6$-alkyl group, $C_1$–$C_6$-alkoxy group, $C_1$–$C_6$-aminoalkyl group, $C_1$–$C_6$-hydroxyalkyl group, a $C_1$–$C_6$-alkoxy-$C_1$–$C_6$-alkyloxy group, a $C_2$–$C_6$-acyl group, an acetyl group, carboxyl group, carboxylato group, carbamoyl group, sulfo group, sulfato group, sulfonamide group, sulfonamido group, $C_2$–$C_6$-alkenyl group, an aryl group, an aryl-$C_1$–$C_6$-alkyl group, a hydroxy group, a nitro group, a pyrrolidino group, a morpholino group, a piperidino group, an amino group and ammonio group or a 1-imidazol(in)io group, where the last three groups may be substituted by one or more $C_1$–$C_6$-alkyl groups, $C_1$–$C_6$-carboxyalkyl groups, $C_1$–$C_6$-hydroxyalkyl groups, $C_2$–$C_6$-alkenyl groups, $C_1$–$C_6$- alkoxy-$C_1$–$C_6$-alkyl groups, with optionally substituted benzyl groups, by sulfo-($C_1$–$C_4$)-alkyl or heterocycle-($C_1$–$C_4$)-alkyl groups, where also two of the radicals from $R^4$, $R^5$, $R^6$ and -Z-Y—$R^3$, together with the radical molecule, can form a fused-on optionally substituted 5-, 6- or 7-membered ring, which can likewise carry a fused-on aromatic ring, where the system AR can, depending on the size of the ring, carry further substituents which, independently of one another, can be the same groups as $R^4$, $R^5$ and $R^6$, Z is a direct bond, a carbonyl group, a carboxy-($C_1$–$C_4$)-alkylene group, an optionally substituted $C_2$–$C_6$-alkenylene group, $C_4$–$C_6$-alkadienylene group, furylene group, thienylene group, arylene group, vinylenearylene group, vinylenefurylene group, vinylenethienylene group, where Z, together with the —Y—$R^3$ group, can also form an optionally substituted 5-, 6- or 7-membered ring, Y is a group which is chosen from carbonyl, a group according to formula (Ox2) and a group according to formula (Ox3)

where
$R^7$ is a hydrogen atom, a hydroxy group, a $C_1$–$C_4$-alkoxy group, a $C_1$–$C_6$-alkyl group, a $C_1$–$C_6$-hydroxyalkyl group, a $C_2$–$C_6$-polyhydroxyalkyl group, a $C_1$–$C_6$-alkoxy-$C_1$–$C_6$-alkyl group, $R^8$ and $R^9$, independently of one another, are a hydrogen atom, a $C_1$–$C_6$-alkyl group, an aryl group or jointly, together with the structural element O—C—O of the formula (Ox3), form a 5- or 6-membered ring.

Component A is particularly preferably chosen from the group consisting of acetophenone, propiophenone, 2-hydroxyacetophenone, 3-hydroxyacetophenone, 4-hydroxyacetophenone, 2-hydroxypropiophenone, 3-hydroxypropiophenone, 4-hydroxypropiophenone, 2-hydroxybutyrophenone, 3-hydroxybutyrophenone, 4-hydroxybutyrophenone, 2,4-dihydroxyacetophenone, 2,5-dihydroxyacetophenone, 2,6-dihydroxyacetophenone, 2,3,4-trihydroxyacetophenone, 3,4,5-trihydroxyacetophenone, 2,4,6-trihydroxyacetophenone, 2,4,6-trimethoxyacetophenone, 3,4,5-trimethoxyacetophenone, 3,4,5-trimethoxyacetophenone diethyl ketal, 4-hydroxy-3-methoxyacetophenone, 3,5-dimethoxy-4-hydroxyacetophenone, 4-aminoacetophenone, 4-dimethylaminoacetophenone, 4-morpholinoacetophenone, 4-piperidinoacetophenone, 4-imidazolinoacetophenone, 2-hydroxy-5-bromoacetophenone, 4-hydroxy-3-nitroacetophenone, acetophenone-2-carboxylic acid, acetophenone-4-carboxylic acid, benzophenone, 4-hydroxybenzophenone, 2-aminobenzophenone, 4,4'-dihydroxybenzophenone, 2,4-dihydroxybenzophenone, 2,4,4'-trihydroxybenzophenone, 2,3,4-trihydroxybenzophenone, 2-hydroxy-1-acetonaphthone, 1-hydroxy-2-acetonaphthone, chromone, chromone-2-carboxylic acid, flavone, 3-hydroxyflavone, 3,5,7-trihydroxyflavone, 4,5,7-trihydroxyflavone, 5,6,7-trihydroxyflavone, quercetin, 1-indanone, 9-fluorenone, 3-hydroxyfluorenone, anthrone, 1,8-dihydroxyanthrone, vanillin, coniferyl aldehyde, 2-methoxybenzaldehyde, 3-methoxybenzaldehyde, 4-methoxybenzaldehyde, 2-ethoxy-benzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-3-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 4-hydroxy-3,5-dimethoxybenzaldehyde, 4-hydroxy-3,5-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-tri-methoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-dihydroxy-5-methylbenzaldehyde, 3,4-dihydroxy-6-methylbenzaldehyde, 3,4-dihydroxy-2-methoxybenzaldehyde, 3,4-dihydroxy-5-methoxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 3,4,5-trihydroxybenzaldehyde, 2,5,6-trihydroxybenzaldehyde, 4-hydroxy-2-methoxybenzaldehyde, 4-dimethylaminobenzaldehyde, 4-diethylaminobenzaldehyde, 4-dimethylamino-2-hydroxybenzaldehyde, 4-diethylamino-2-hydroxybenzaldehyde, 4-pyrrolidinobenzaldehyde, 4-morpholinobenzaldehyde, 2-morpholinobenzaldehyde, 4-piperidinobenzaldehyde, 2-methoxy-1-naphthaldehyde, 4-methoxy-1-naphthaldehyde, 2-hydroxy-1-naphthaldehyde, 2,4-dihydroxy-1-naphthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-hydroxy-1-naphthaldehyde, 4-dimethylamino-1-naphthaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylaminobenzaldehyde, 4-dimethylamino-2-methoxybenzaldehyde, 4-(1-imidazolyl)benzaldehyde, piperonal, 2,3,6,7-tetrahydro-1H,5H-benzo[ij]quinolizine-9-carboxaldehyde, 2,3,6,7-tetrahydro-8-hydroxy-1H,5H-benzo[ij]quinolizine-9-carboxaldehyde, N-ethylcarbazole-3-aldehyde, 2-formylmethylene-1,3,3-trimethylindoline (Fischers aldehyde or tribase aldehyde), 2-indolealdehyde, 3-indolealdehyde, 1-methylindole-3-aldehyde, 2-methylindole-3-aldehyde, 1-acetylindole-3-aldehyde, 3-acetylindole, 1-methyl-3-acetylindole, 2-(1',3',3'-trimethyl-2-indolinylidene)acetaldehyde, 1-methylpyrrole-2-aldehyde, 1-methyl-2-acetylpyrrole, 4-pyridinealdehyde, 2-pyridinealdehyde, 3-pyridinealdehyde, 4-acetylpyridine, 2-acetylpyridine, 3-acetylpyridine, pyridoxal, quinoline-3-aldehyde, quinoline-4-aldehyde, antipyrine-4-aldehyde, furfural, 5-nitrofurfural, 2-theonyltrifluoroacetone, chromone-3-aldehyde, 3-(5'-nitro-2'-furyl)acrolein, 3-(2'-furyl)acrolein and imidazole-2-aldehyde, 1,3-diacetylbenzene, 1,4-diacetylbenzene, 1,3,5-triacetyl-benzene, 2-benzoylacetophenone, 2-(4'-methoxybenzoyl)acetophenone, 2-(2'-furoyl)acetophenone, 2-(2'-pyridoyl)acetophenone and 2-(3'-pyridoyl)acetophenone, benzylidene acetone, 4-hydroxybenzylidene acetone, 2-hydroxybenzylidene acetone, 4-methoxybenzylidene acetone, 4-hydroxy-3-methoxybenzylidene acetone, 4-dimethylaminobenzylidene acetone, 3,4'-methylenedioxybenzylidene acetone, 4-pyrrolidinobenzylidene acetone, 4-piperidinobenzylidene acetone, 4-morpholinobenzylidene acetone, 4-diethylaminobenzylidene acetone, 3-benzylidene-2,4-pentanedione, 3-(4'-hydroxy-benzylidene)-2,4-pentanedione, 3-(4'-dimethylaminobenzylidene)-2,4-pentanedione, 2-benzylidenecyclohexanone, 2-(4'-hydroxybenzylidene)cyclohexanone, 2-(4'-dimethylaminobenzylidene)cyclohexanone, 2-benzylidene-1,3-cyclohexanedione, 2-(4'-hydroxybenzylidene)-1,3-cyclohexanedione, 3-(4'-dimethylaminobenzylidene)-1,3-cyclohexanedione, 2-benzylidene-5,5-dimethyl-1,3-cyclohexanedione, 2-(4'-hydroxybenzylidene)-5,5-dimethyl-1,3-cyclohexanedione, 2-(4'-hydroxy-3-methoxybenzylidene)-5,5-dimethyl-1,3-cyclohexanedione, 2-(4'-dimethylaminobenzylidene)-5,5-dimethyl-1,3-cyclohexanedione, 2-benzylidenecyclopentanone, 2'-(4-hydroxybenzylidene)cyclopentanone, 2-(4'-dimethylaminobenzylidene)cyclopentanone, 5-(4-di-methylaminophenyl)penta-2,4-dienal, 5-(4-diethylamino-phenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 6-(4-dimethylaminophenyl)hexa-3,5-dien-2-one, 6-(4-diethyl-aminophenyl)hexa-3,5-dien-2-one, 6-(4-methoxyphenyl)hexa-3,5-dien-2-one, 6-(3,4-dimethoxyphenyl)hexa-3,5-dien-2-one, 6-(2,4-dimethoxyphenyl)hexa-3,5-dien-2-one, 6-(4-piperidinophenyl)hexa-3,5-dien-2-one, 6-(4-morpholinophenyl)hexa-3,5-dien-2-one, 6-(4-pyrrolidinophenyl)hexa-3,5-dien-2-one, 5-(4-dimethylamino-1-naphthyl)penta-3,5-dienal, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 4-hydroxy-3-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitropiperonal, 2-nitropiperonal, 5-nitrovanillin, 2,5-dinitrosalicylaldehyde, 5-bromo-2-nitrosalicylaldehyde, 3-nitro-4-formylbenzenesulfonic acid, 4-nitro-1-naphthaldehyde, 2-nitrocinnamaldehyde, 3-nitrocinnamaldehyde, 4-nitrocinnamaldehyde, 9-methyl-3-carbazolealdehyde, 9-ethyl-3-carbazolealdehyde, 3-acetylcarbazole, 3,6-diacetyl-9-ethylcarbazole, 3-acetyl-9-methylcarbazole, 1,4-dimethyl-3-carbazolealdehyde, 1,4,9-trimethyl-3-carbazolealdehyde, 4-formyl-1-methylpyridinium, 2-formyl-1-methylpyridinium, 4-formyl-1-ethylpyridinium, 2-formyl-1-ethylpyridinium, 4-formyl-1-benzylpyridinium, 2-formyl-1-benzylpyridinium, 4-formyl-1,2-dimethylpyridinium, 4-formyl-1,3-dimethylpyridinium, 4-formyl-1-methylquinolinium, 2-formyl-1-methylquinolinium, 4-acetyl-1-methylpyridinium, 2-acetyl-1-methylpyridinium, 4-acetyl-1-methylquinolinium, 5-formyl-1-methylquinolinium, 6-formyl-1-methylquinolinium, 7-formyl-1-methylquinolinium, 8-formyl-1-methylquinolinium, 5-formyl-1-ethylquinolinium, 6-formyl-1-ethylquinolinium, 7-formyl-1-ethylquinolinium, 8-formyl-1-ethylquinolinium, 5-formyl-1-benzylquinolinium, 6-formyl-1-benzylquinolinium, 7-formyl-1-benzylquinolinium, 8-formyl-1-benzylquinolinium, 5-formyl-1-allylquinolinium, 6-formyl-1-allylquinolinium, 7-formyl-1-allylquinolinium and 8-formyl-1-allylquinolinium, 5-acetyl-1-methylquinolinium, 6-acetyl-1-methylquinolinium, 7-acetyl-1-methylquinolinium, 8-acetyl-1-methylquinolinium, 5-acetyl-1-ethylquinolinium, 6-acetyl-1-ethylquinolinium, 7-acetyl-1-ethylquinolinium, 8-acetyl-1-ethylquinolinium, 5-acetyl-1-benzylquinolinium, 6-acetyl-1-benzylquinolinium, 7-acetyl-1-benzylquinolinium, 8-acetyl-1-benzylquinolinium, 5-acetyl-1-allylquinolinium, 6-acetyl-1-allylquinolinium, 7-acetyl-1-allylquinolinium and 8-acetyl-1-allylquinolinium, 9-formyl-10-methylacridinium, 4-(2'-formylvinyl)-1-methylpyridinium, 1,3-dimethyl-2-(4'-formylphenyl)benzimidazolium, 1,3-dimethyl-2-(4'-formylphenyl)-imidazolium, 2-(4'-formylphenyl)-3-methylbenzothiazolium, 2-(4'-acetylphenyl)-3-methylbenzothiazolium, 2-(4'-formylphenyl)-3-methylbenzoxazolium, 2-(5'-formyl-2'-furyl)-3-methylbenzothiazolium, 2-(5'-formyl-2'-furyl)-3-methylbenzothiazolium, 2-(5'-formyl-2'-thienyl)-3-methylbenzothiazolium, 2-(3'-formylphenyl)-3-methylbenzothiazolium, 2-(4'-formyl-1-naphthyl)-3-methylbenzothiazolium, 5-chloro-2-(4'-formylphenyl)-3-methylbenzothiazolium, 2-(4'-formyl-1-naphthyl)-3-methylbenzothiazolium, 5-chloro-2-(4'-formylphenyl)-3-methylbenzothiazolium, 2-(4'-formylphenyl)-3,5-dimethylbenzothiazolium benzenesulfonate, p-toluenesulfonate, methanesulfonate, perchlorate, sulfate, chloride, bromide, iodide, tetrachlorozincate, methylsulfate, trifluoromethanesulfonate, tetrafluoroborate, isatin, 1-methylisatin, 1-allylisatin, 1-hydroxymethylisatin, 5-chloroisatin, 5-methoxyisatin, 5-nitroisatin, 6-nitroisatin, 5-sulfoisatin, 5-carboxyisatin, quinisatin, 1-methylquinisatin, and any mixtures of the above compounds.

In the compositions according to the invention, very particular preference is given to using benzaldehyde, cinnamaldehyde and naphthaldehyde, and derivatives thereof, in particular with one or more hydroxy, alkoxy or amino substituents as component A. In turn, preference is given here to the compounds according to formula (Ox4),

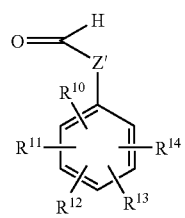

(Ox4)

in which

R$^{10}$, R$^{11}$ and R$^{12}$, independently of one another, are a hydrogen atom, a halogen atom, a C$_1$–C$_6$-alkyl group, a hydroxy group, a $C_1$–$C_6$-alkoxy group, an amino group, a $C_1$–$C_6$-dialkylamino group, a di($C_2$–$C_6$-hydroxyalkyl) amino group, a di($C_1$–$C_6$-alkoxy-$C_1$–$C_6$-alkyl)amino group, a $C_1$–$C_6$-hydroxyalkyloxy group, a sulfonyl group, a carboxyl group, a sulfonic acid group, a sulfonamido group, a sulfonamide group, a carbamoyl group, a $C_2$–$C_6$-acyl group, an acetyl group or a nitro group, Z' is a direct bond or a vinylene group, $R^{13}$ and $R^{14}$ are a hydrogen atom or jointly, together with the remaining molecule, form a 5- or 6-membered aromatic or aliphatic ring.

Very particularly preferred compounds of component A are chosen from the group consisting of vanillin, coniferylaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-3-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 4-hydroxy-3,5-dimethoxybenzaldehyde, 4-hydroxy-3,5-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxy-benzaldehyde, 3,4-dimethoxybenzaldehyde, 3,5-dimethoxy-benzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-dihydroxy-5-methylbenzaldehyde, 3,4-dihydroxy-6-methylbenzaldehyde, 3,4-dihydroxy-2-methoxybenzaldehyde, 3,4-dihydroxy-5-methoxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-tri-hydroxybenzaldehyde, 2,4,5-trihydroxybenzaldehyde, 2,5,6-trihydroxybenzaldehyde, 3,4,5-trihydroxybenzaldehyde, 4-hydroxy-2-methoxybenzaldehyde, 4-dimethylaminobenzaldehyde, 4-diethylaminobenzaldehyde, 4-dimethylamino-2-hydroxybenzaldehyde, 4-diethylamino-2-hydroxybenzaldehyde, 4-pyrrolidinobenzaldehyde, 4-morpholinobenzaldehyde, 2-morpholinobenzaldehyde, 4-piperidinobenzaldehyde, 2-methoxy-1-naphthaldehyde, 4-methoxy-1-naphthaldehyde, 2-hydroxy-1-naphthaldehyde, 2,4-dihydroxy-1-naphthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-hydroxy-1-naphthaldehyde, 4-dimethylamino-1-naphthaldehyde, 4-dimethylaminocinnamaldehyde, 2-dimethyl-aminobenzaldehyde, 2-chloro-4-dimethylaminobenzaldehyde, 4-dimethylamino-2-methylbenzaldehyde, 4-diethyl-aminocinnamaldehyde, 4-dibutylaminobenzaldehyde, 4-diphenylaminobenzaldehyde, 4-dimethylamino-2-methoxybenzaldehyde, 4-(1-imidazolyl)benzaldehyde and piperonal.

In a second embodiment, in order to expand the color spectrum and also to improve the fastness properties, it may be advantageous to add to the compositions, besides the reactive carbonyl compound (component A), at least one further compound as component B chosen from (a) CH-acidic compounds and (b) compounds with a primary or secondary amino or hydroxy group, chosen from aromatic hydroxy compounds, primary or secondary aromatic amines and nitrogen-containing heterocyclic compounds. CH-acidic compounds have an acidic hydrogen atom bonded to a carbon atom which can be abstracted from the carbon atom using a base.

The CH-acidic compounds of component B are preferably chosen from the group consisting of 1,2,3,3-tetramethyl-3H-indolium iodide, 1,2,3,3-tetramethyl-3H-indolium p-toluenesulfonate, 1,2,3,3-tetramethyl-3H-indolium methanesulfonate, 1,3,3-trimethyl-2-methyleneindoline (Fischer's base), 2,3-dimethylbenzothiazolium iodide, 2,3-dimethylbenzothiazolium p-toluenesulfonate, 2,3-dimethylnaphtho[1,2-d]thiazolium p-toluenesulfonate, 3-ethyl-2-methylnaphtho-[1,2-d]thiazolium p-toluenesulfonate, rhodanine, rhodanine-3-acetic acid, 1,4-dimethylquinolinium iodide, 1,2-dimethylquinolinium iodide, barbituric acid, thiobarbituric acid, 1,3-dimethylthiobarbituric acid, 1,3-diethylthiobarbituric acid, 1,3-diethylbarbituric acid, oxindole, 3-indoxyl acetate, 2-coumaranone, 5-hydroxy-2-coumaranone, 6-hydroxy-2-coumaranone, 3-methyl-1-phenylpyrazolin-5-one, indan-1,2-dione, indane-1,3-dione, indane-1-one, benzoylacetonitrile, 3-dicyanomethyleneindan-1-one, 2-amino-4-imino-1,3-thiazoline hydrochloride, 5,5-dimethylcyclohexane-1,3-dione, 2H-1,4-benzoxazin-4H-3-one, 3-ethyl-2-methylbenzoxazolium iodide, 3-ethyl-2-methylbenzothiazolium iodide, 1-ethyl-4-methylquinolinium iodide, 1-ethyl-2-methylquinolinium iodide, 1,2,3-trimethylquinoxalinium iodide, 3-ethyl-2-methylbenzoxazolium p-toluenesulfonate, 3-ethyl-2-methylbenzothiazolium p-toluenesulfonate, 1-ethyl-4-methylquinolinium p-toluenesulfonate, 1-ethyl-2-methylquinolinium p-toluenesulfonate, 1,2,3-trimethylquinoxalinium p-toluenesulfonate, 1,2-dihydro-1,3,4,6-tetramethyl-2-oxopyrimidinium chloride, 1,2-dihydro-1,3,4,6-tetramethyl-2-oxopyrimidinium hydrogensulfate, 1,2-dihydro-1,3,4-trimethyl-2-oxopyrimidinium chloride, 1,2-dihydro-4,6-dimethyl-1,3-dipropyl-2-oxopyrimidinium chloride, 1,2-dihydro-1,3,4,6-tetramethyl-2-thioxopyrimidinium hydrogensulfate and 2-dihydro-1,3,4,5,6-pentamethyl-2-oxopyrimidinium chloride.

The primary and secondary aromatic amines of component B are preferably chosen from the group consisting of N,N-dimethyl-p-phenylenediamine, N,N-diethyl-p-phenylenediamine, N-(2-hydroxyethyl)-N-ethyl-p-phenylenediamine, N,N-bis(2-hydroxyethyl)-p-phenylenediamine, N-(2-methoxyethyl)-p-phenylenediamine, 2,3-dichloro-p-phenylenediamine, 2,4-dichloro-p-phenylenediamine, 2,5-dichloro-p-phenylenediamine, 2-chloro-p-phenylenediamine, 2,5-dihydroxy-4-morpholinoaniline, 2-aminophenol, 3-aminophenol, 4-aminophenol, 2-aminomethyl-4-aminophenol, 2-hydroxymethyl-4-aminophenol, o-phenylenediamine, m-phenylenediamine, p-phenylenediamine, 2,5-diaminotoluene, 2,5-diaminophenol, 2,5-diaminoanisole, 2,5-diaminophenethol, 4-amino-3-methylphenol, 2-(2,5-diaminophenyl)ethanol, 2,4-diaminophenoxyethanol, 2-(2,5-diaminophenoxy)ethanol, 3-amino-4-(2- hydroxyethyloxy)phenol, 3,4-methylenedioxyphenol, 3,4-methylenedioxyaniline, 3-amino-2,4-dichlorophenol, 4-methyl-aminophenol, 2-methyl-5-aminophenol, 3-methyl-4-aminophenol, 2-methyl-5-(2-hydroxyethylamino) phenol, 3-amino-2-chloro-6-methylphenol, 2-methyl-5-amino-4-chlorophenol, 5-(2-hydroxy-ethylamino)-4-methoxy-2-methylphenol, 4-amino-2-hydroxymethylphenol, 2-(diethylaminomethyl)-4-aminophenol, 4-amino-1-hydroxy-2-(2-hydroxyethylaminomethyl)benzene, 1-hydroxy-2-amino-5-methylbenzene, 1-hydroxy-2-amino-6-methylbenzene, 2-amino-5-acetamidophenol, 1,3-dimethyl-2,5-diaminobenzene, 5-(3-hydroxypropylamino)-2-methylphenol, 5-amino-4-methoxy-2-methylphenol, N,N-dimethyl-3-aminophenol, N-cyclopentyl-3-aminophenol, 5-amino-4-fluoro-2-methylphenol, 2,4-diamino-5-fluorotoluene, 2,4-diamino-5-(2-hydroxyethoxy)toluene, 2,4-diamino-5-methylphenetol, 3,5-diamino-2-methoxy-1-methylbenzene, 2-amino-4-(2-hydroxyethylamino)anisole, 2,6-bis(2-hydroxyethylamino)-1-methylbenzene, 1,3-diamino-2,4-dimethoxy-benzene, 3,5-diamino-2-methoxytoluene, 2-aminobenzoic acid, 3-aminobenzoic acid, 4-aminobenzoic acid, 2-aminophenylacetic acid, 3-aminophenylacetic acid, 4-aminophenylacetic acid, 2,3-diaminobenzoic acid, 2,4-diaminobenzoic acid, 2,5-diaminobenzoic acid, 3,4-diaminobenzoic acid, 3,5-diaminobenzoic acid, 4-aminosalicylic acid, 5-aminosalicylic acid, 3-amino-4-hydroxybenzoic acid, 4-amino-3-hydroxybenzoic acid, 2-aminobenzenesulfonic acid, 3-aminobenzenesulfonic acid, 4-aminobenzenesulfonic acid, 3-amino-4-hydroxybenzenesulfonic acid, 4-amino-3-hydroxynaphthalene-1-sulfonic acid, 6-amino-7-hydroxynaphthalene-2-sulfonic acid, 7-amino-4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechin, 4,6-diaminopyrogallol, 1-(2-hydroxy-5-aminobenzyl)-2-imidazolidinone, 4-amino-2-((4-[(5-amino-2-hydroxyphenyl)methyl]piperazinyl)-methyl) phenol, 3,5-diamino-4-hydroxypyrocatechin, 1,4-bis(4-aminophenyl)-1,4-diazacycloheptane, aromatic nitriles, such as 2-amino-4-hydroxybenzonitrile, 4-amino-2-hydroxybenzonitrile, 4-aminobenzonitrile, 2,4-diaminobenzonitrile, amino compounds containing nitro groups, such as 3-amino-6-methylamino-2-nitro-pyridine, picramic acid, [8-[(4-amino-2-nitrophenyl)azo]-7-hydroxynaphth-2-yl]trimethylammonium chloride, [8-((4-amino-3-nitrophenyl)azo)-7-hydroxynaphth-2-yl]trimethylammonium chloride (Basic Brown 17), 1-hydroxy-2-amino-4,6-dinitrobenzene, 1-amino-2-nitro-4-[bis(2-hydroxyethyl)amino]benzene, 1-amino-2-[(2-hydroxyethyl)amino]-5-nitrobenzene (HC Yellow No. 5), 1-amino-2-nitro-4-[(2-hydroxyethyl)amino] benzene (HC Red No. 7), 2-chloro-5-nitro-N-2-hydroxyethyl-1,4-phenylenediamine, 1-[(2-hydroxyethyl)amino]-2-nitro-4-aminobenzene (HC Red No. 3), 4-amino-3-nitrophenol, 4-amino-2-nitrophenol, 6-nitro-o-toluidine, 1-amino-3-methyl-4-[(2-hydroxyethyl)amino]-6-nitrobenzene (HC Violet No. 1), 1-amino-2-nitro-4-[(2,3-dihydroxypropyl)amino]-5-chlorobenzene (HC Red No. 10), 2-(4-amino-2-nitroanilino)benzoic acid, 6-nitro-2,5-diaminopyridine, 2-amino-6-chloro-4-nitrophenol, 1-amino-2-(3-nitrophenylazo)-7-phenylazo-8-naphthol-3,6-disulfonic acid disodium salt (Acid Blue No. 29), 1-amino-2-(2-hydroxy-4-nitrophenylazo)-8-naphthol-3,6-disulfonic acid disodium salt (palatine chrome green), 1-amino-2-(3-chloro-2-hydroxy-5-nitrophenylazo)-8-naphthol-3,6-disulfonic acid disodium salt (Gallion), 4-amino-4'-nitrostilbene-2,2'-disulfonic acid disodium salt, 2,4-diamino-3',5'-dinitro-2'-hydroxy-5-methylazobenzene (Mordant Brown 4), 4'-amino-4-nitrodiphenylamine-2-sulfonic acid, 4'-amino-3'-nitro-benzophenone-2-carboxylic acid, 1-amino-4-nitro-2-(2-nitro-benzylideneamino)benzene, 2-[2-(diethylamino) ethylamino]-5-nitroaniline, 3-amino-4-hydroxy-5-nitrobenzenesulfonic acid, 3-amino-3'-nitrobiphenyl, 3-amino-4-nitroacenaphthene, 2-amino-1-nitronaphthalene, 5-amino-6-nitrobenzo-1,3-dioxole, anilines, in particular anilines containing nitro groups, such as 4-nitroaniline, 2-nitroaniline, 1,4-diamino-2-nitrobenzene, 1,2-diamino-4-nitrobenzene, 1-amino-2-methyl-6-nitrobenzene, 4-nitro-1,3-phenylenediamine, 2-nitro-4-amino-1-(2-hydroxyethylamino)benzene, 2-nitro-1-amino-4-[bis(2-hydroxyethyl) amino]benzene, 4-amino-2-nitrodiphenylamine-2'-carboxylic acid, 1-amino-5-chloro-4-(2-hydroxyethylamino)-2-nitrobenzene, aromatic anilines and phenols with a further aromatic radical as shown in formula (Ox5)

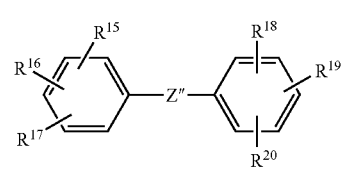

(Ox5)

in which $R^{15}$ is a hydroxy or an amino group which may be substituted by $C_1$–$C_6$-alkyl, $C_1$–$C_6$-hydroxyalkyl, $C_1$–$C_6$-alkoxy or $C_1$–$C_6$-alkoxy-$C_1$–$C_6$-alkyl groups, $R^{16}$, $R^{17}$, $R^{18}$, $R^{19}$ and $R^{20}$, independently of one another, are a hydrogen atom, a hydroxy or an amino group which may be substituted by $C_1$–$C_6$-alkyl, $C_1$–$C_6$-hydroxyalkyl, $C_1$–$C_6$-alkoxy, $C_1$–$C_6$-aminoalkyl or $C_1$–$C_6$-alkoxy-$C_1$–$C_6$-alkyl groups, and Z" is a direct bond, a saturated or unsaturated carbon chain optionally substituted by hydroxy groups and having 1 to 4 carbon atoms, a carbonyl group, sulfonyl group or imino group, an oxygen atom or sulfur atom, or a group with the formula (Ox6)

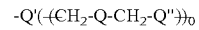

(Ox6)

in which

Q is a direct bond, a $CH_2$ group or CHOH group,

Q' and Q", independently of one another, are an oxygen atom, an $NR^{21}$ group, in which $R^{21}$ is a hydrogen atom, a $C_1$–$C_6$-alkyl group or $C_1$–$C_6$-hydroxyalkyl group, where also the two groups, together with the remaining molecule, can form a 5-, 6- or 7-membered ring, the group O—$(CH_2)_p$—NH or NH—$(CH_2)_{p'}$—O, in which p and p' are 2 or 3, and o is a number from 1 to 4, such as, in particular, 4,4'-diaminostilbene and its hydrochloride, 4,4'-diaminostilbene-2,2'-disulfonic acid mono- or di-Na salt, 4-amino-4'-dimethylaminostilbene and its hydrochloride, 4,4'-diaminodiphenylmethane, 4,4'-diaminodiphenyl sulfide, 4,4'-diaminodiphenyl sulfoxide, 4,4'-diaminodiphenylamine, 4,4'-diaminodiphenylamine-2-sulfonic acid, 4,4'-diaminobenzophenone, 4,4'-diaminodiphenyl ether, 3,3',4,4'-tetraaminodiphenyl, 3,3',4,4'-tetraaminobenzophenone, 1,3-bis(2,4-diaminophenoxy)propane, 1,8-bis(2,5-diaminophenoxy)-3,6-dioxaoctane, 1,3-bis(4-aminophenylamino)propane, 1,3-bis(4-aminophenylamino)-2-propanol, 1,3-bis[N-(4-aminophenyl)-2-hydroxyethylamino]-2-propanol, N,N-bis[2-(4-aminophenoxy)ethyl]-methylamine, N-phenyl-1,4-phenylenediamine and bis(5-amino-2-hydroxyphenyl)methane.

The nitrogen-containing heterocyclic compounds of component B are preferably chosen from the group consisting of 2-aminopyridine, 3-aminopyridine, 4-aminopyridine, 2-amino-3-hydroxypyridine, 2,6-diaminopyridine, 2,5-diaminopyridine, 2-(aminoethylamino)-5-aminopyridine, 2,3-diaminopyridine, 2-di-methylamino-6-aminopyridine, 2-methylamino-3-amino-6-methoxypyridine, 2,3-diamino-6-methoxypyridine, 2,6-dimethoxy-3,5-diaminopyridine, 2,4,5-triaminopyridine, 2,6-dihydroxy-3,4-dimethylpyridine, N-[2-(2,4-diaminophenyl)aminoethyl]-N-(5-amino-2-pyridyl)amine, N-[2-(4-aminophenyl)aminoethyl]-N-(5-amino-2-pyridyl)amine, 2,4-dihydroxy-5,6-diaminopyrimidine, 4,5,6-triaminopyrimidine, 4-hydroxy-2,5,6-triaminopyrimidine, 2-hydroxy-4,5,6-triaminopyrimidine, 2,4,5,6-tetraaminopyrimidine, 2-methylamino-4,5,6-triaminopyrimidine, 2,4-diaminopyrimidine, 4,5-diaminopyrimidine, 2-amino-4-methoxy-6-methylpyrimidine, 3,5-diaminopyrazole, 3,5-diamino-1,2,4-triazole, 3-aminopyrazole, 3-amino-5-hydroxypyrazole, 1-phenyl-4,5-diaminopyrazole, 1-(2-hydroxyethyl)-4,5-diaminopyrazole, 1-phenyl-3-methyl-4,5-diaminopyrazole, 4-amino-2,3-dimethyl-1-phenyl-3-pyrazolin-5-one (4-aminoantipyrin), 1-phenyl-3-methyl-pyrazol-5-one, 2-aminoquinoline, 3-aminoquinoline, 8-aminoquinoline, 4-aminoquinaldin, 2-aminonicotinic acid, 6-aminonicotinic acid, 5-aminoisoquinoline, 5-aminoindazole, 6-aminoindazole, 5-aminobenzimidazole, 7-aminobenzimidazole, 5-aminobenzothiazole, 7-aminobenzothiazole, 2,5-dihydroxy-4-morpholinoaniline, and indole and indoline derivatives, such as 4-aminoindole, 5-aminoindole, 6-aminoindole, 7-aminoindole, 5,6-dihydroxyindole, 5,6-dihydroxyindoline and 4-hydroxyindoline. In addition, heterocyclic compounds which can be used according to the invention are the hydroxypyrimidines disclosed in DE-U1-299 08 573. The abovementioned compounds can be used either in free form or else in the form of their physiologically compatible salts, e.g. as salts of inorganic acids, such as hydrochloric acid or sulfuric acid.

The aromatic hydroxy compounds of component B are preferably chosen from the group consisting of 2-methylresorcinol, 4-methylresorcinol, 5-methylresorcinol, 2,5-dimethylresorcinol, resorcinol, 3-methoxyphenol, pyrocatechin, hydroquinone, pyrogallol, phloroglucine, hydroxyhydroquinone, 2-methoxyphenol, 3-methoxyphenol, 4-methoxyphenol, 3-dimethylaminophenol, 2-(2-hydroxyethyl)phenol, 3,4-methylenedioxyphenol, 2,4-dihydroxybenzoic acid, 3,4-dihydroxybenzoic acid, 1-(2,4-dihydroxyphenyl)acetic acid, 1-(3,4-dihydroxyphenyl)acetic acid, gallic acid, 2,4,6-trihydroxybenzoic acid, -acetophenone, 2-chlororesorcinol, 4-chlororesorcinol, 1-naphthol, 1,5-dihydroxynaphthalene, 2,3-dihydroxynaphthalene, 2,7-dihydroxynaphthalene, 6-dimethylamino-4-hydroxy-2-naphthalenesulfonic acid and 3,6-dihydroxy-2,7-naphthalenesulfonic acid.

In a further preferred embodiment, the cosmetic preparations are in the form of a liquid, preferably in the form of a dispersion, emulsion, solution or gel, particularly preferably with a viscosity of from 500 to 4000 mPas, more preferably 5000 to 35 000 mPas, in particular from 10 000 to 35 000 mPas, specifically from 20 000 to 32 000 mPas (Brookfield viscometer LVT-II at 4 rpm and 20° C., spindle 5).

As already described above, the cosmetic preparations preferably have a water content below 20% by weight, preferably below 12% by weight, particularly preferably below 8% by weight, further preferably below 4% by weight, in particular below 2% by weight, in each case based on the total cosmetic preparation.

The liquid coloring systems known from the prior art for keratin materials comprise, as solvent, virtually exclusively water or mixtures of water with low molecular weight alcohols such as ethanol and/or isopropanol. When choosing these solvents, physiological factors firstly play a role, and secondly coloration of the inside of the hair is ensured only with suitable transport media, and a reaction in the case of systems capable of reaction is ensured only with a suitable reaction medium. These conditions are optimally satisfied with water or water/alcohol mixtures. The use of the cited solvents, however, is not only associated with advantages. Upon storage in aqueous or aqueous-alcoholic media, some dyes undergo hydrolysis or dissolve only inadequately. These disadvantages can be overcome in principle through storage in, for example, powder form. However, this type of preparation does not always represent an optimum solution. For example, the finely divided dispersion necessary for extensive dissolving of all components is often not ensured.

In a further preferred embodiment, the hair colorants or hair colorant precursors, in particular component A of the oxo hair colorants, have a solubility in water below 5% by weight, preferably below 2% by weight, in particular below 1% by weight.

Suitable sparingly water-soluble hair colorant precursors are known from the German published specification DE 2932489, which discloses aromatic aldehydes, and from the German patent application DE 196 30 275, which describes vinylogs, aromatic aldehydes. The specified publications describe numerous compounds which only have a limited solubility in water of less than 1 g/l (20° C.). Particular preference is given to the isatin derivatives known from WO 95/24886. Dyes which are chosen from the group of isatin derivatives or of aromatic or vinylog carbonyl compounds are particularly preferred since these dyes are often sparingly soluble in water. These dye precursors are often used for the oxo coloration. Particularly preferred cosmetic preparations comprise 1-allylisatin, 1-diethylaminomethylisatin, 1-diethylaminomethylisatin, 1-piperidinomethylisatin, 4-hydroxy-3-methoxycinnamaldehyde, glutaconaldehyde tetrabutylammonium salt and 2-(1,3,3-trimethyl-2-indolylidene)acetaldehyde.

The dyes or dye precursors preferably have good solubility in oil. For the purposes of the present embodiment according to the invention, oil-soluble substances are understood as meaning substances whose solubility in paraffin oil at 20° C. is above 0.1% by weight.

It has been found that especially for the preparation of low-water cosmetic preparations, in particular low-water hair colorant preparations, oils can additionally be used. Preference is given to using liquid oil components.

Liquid oil components for the purposes of the present embodiment according to the invention are all physiologically compatible mineral, animal, vegetable or synthetic oil components which are liquid at 20° C. Examples of such oil components are, for example, paraffin oils, silicone oils, triglyceride oils, e.g. neatsfoot oil, lard oil, mink oil, olive oil, sunflower oil, almond oil, liquid wax esters, such as, for example, sperm oil, jojoba oil, synthetic esters, such as, for example, glycerol tricaprylate, n-hexyl laurate, isopropyl myristate, 2-ethylhexyl stearate, butyl oleate, synthetic ethers, such as, for example, di-n-octyl ether, synthetic hydrocarbons, such as, for example, diisooctylcyclohexane, squalane, synthetic alcohols, such as, for example, 2-octyldodecanol or 2-hexyldecanol.

The cosmetic preparations particularly preferably additionally comprise an oil chosen from the group
a) mineral oils, preferably paraffin oils,
b) vegetable oils, preferably sunflower oil, rapeseed oil, soybean oil, castor oil,
c) silicone oils, preferably quaternized silicones,
d) esters of $C_{10}$–$C_{36}$-fatty acids, preferably esters of $C_{14}$–$C_{28}$-fatty acids and
e) dialkyl ethers with at least one carbon radical which carries 6 or more carbon atoms.

In a further preferred embodiment, the cosmetic formulations advantageously comprise components which, upon dissolution in water, liberate a greater heat of hydration and, on the basis of the development of heat, in particular with hair colorant preparation, lead to improved color absorption. The cosmetic preparations preferably comprise one or more components with an exothermic solubility behavior in water, preferably chosen from the group
a) alkali metal or alkaline earth metal salts, preferably alkali metal or alkaline earth metal halides and/or sulfates, in particular calcium chloride and/or magnesium sulfate and/or dehydrated zeolites and
b) low molecular weight polyols, preferably glycerol, propylene glycol or polyethylene glycol.

For the anhydrous, preferably oil-containing, cosmetic formulations, it has surprisingly been found that the viscosity build-up, necessary for the stable finely divided dispersing, of nonpolar or semipolar oils can be achieved through various additives. In a preferred embodiment of the present embodiment according to the invention, the cosmetic preparations have one or more viscosity-regulating additives which are chosen from
a) esters or amides of di-, tri-, tetra- or polyols, in particular dextrin mono- or polyesterified with palmitic acid or N-lauroyl-1-glutamic acid, α,γ-di-n-butylamide,
b) esters of di- or oligocarboxylic acids, in particular dibehenylfumaric esters,
c) sheet silicates, preferably organically modified, in particular hydrophobically modified, sheet silicates,
d) mono- or diglycerides of $C_{12}$–$C_{22}$-fatty acids
e) alkali metal, alkaline earth metal and aluminum salts of fatty acids and/or hydroxycarboxylic acids, in particular the lithium salts of $C_3$–$C_{14}$-hydroxycarboxylic acids,
f) aerosils, preferably $SiO_2$ and/or $TiO_2$, particularly preferably those with an average particle size below 100 μm, in particular below 100 μm,
g) polyols, preferably polyethylene glycols and/or polypropylene glycols, particularly preferably polyols with an average molecular weight below 20 000,
h) dibenzylidene sorbitols and derivatives thereof,
i) copolymers with aminodithiazoles,
j) graft copolymers of polyvinylpyridine with sulfonated polyisobutylene,
k) crosslinked polyamines and/or polyimines
l) polymers chosen from i) rubber-based block copolymers, ii) silicone oils with a viscosity above 2000 mPas, iii) microcrystalline waxes and
m) ethylene-vinyl acetate copolymers.

Particularly preferred viscosity-regulating additives for the low-water cosmetic formulations in the portions according to the invention have proven to be dibenzylidene sorbitols and derivatives thereof which are described in U.S. Pat. No. 6,338,841 B1 and whose content is incorporated into the application. Preference is also given to the copolymers with aminodiazoles as described in U.S. Pat. No. 5,472,627 and whose content is explicitly incorporated by reference. Also preferred are graft copolymers of polyvinylpyridine with sulfonated polyisobutylene as described in U.S. Pat. No. 5,328,960 and whose content is incorporated into this application in its entirety. Also preferred are the crosslinked polyamines and/or polyimines as explicitly disclosed in WO 01/46373 A1. Specific preference is likewise given to the esters of di- or oligocarboxylic acids, in particular dibehenylfumaric esters as disclosed in WO 99/51191. Further preferred viscosity-regulating additives are polymers chosen from I) rubber-based block copolymers, II) silicone oils with a viscosity above 2000 mPas, III) microcrystalline waxes as described in WO 98/30193. For the viscosity build-up in low-water hair colorant systems, the lithium salts of $C_3$–$C_{14}$-hydroxycarboxylic acids as described explicitly in WO 98/11180 have proven to be particularly advantageous. It is likewise advantageous to use ethylene-vinyl acetate copolymers as described in WO 97/07158 and whose content is incorporated into this application in its entirety.

The cosmetic preparations can, moreover, comprise further active ingredients and auxiliaries.

In many cases, the colorants comprise at least one surfactant, with, in principle, both anionic and also zwitterionic, ampholytic, nonionic and cationic surfactants being suitable. It has proven to be advantageous to choose the surfactants from anionic, zwitterionic or nonionic surfactants.

Suitable anionic surfactants in preparations are all anionic surface-active substances suitable for use on the human body. These are characterized by a water-solubilizing anionic group such as, for example, a carboxylate, sulfate, sulfonate or phosphate group, and a lipophilic alkyl group having about 10 to 22 carbon atoms. In addition, glycol or polyglycol ether groups, ester groups, ether groups and amide groups and also hydroxyl groups, may be present in the molecule. Examples of suitable anionic surfactants are, in each case in the form of the sodium, potassium and ammonium and also the mono-, di- and trialkanolammonium salts having 2 or 3 carbon atoms in the alkanol group, linear fatty acids having 10 to 22 carbon atoms (soaps),
ether carboxylic acids of the formula R—O—($CH_2$—$CH_2O)_x$—$CH_2$—COOH, in which R is a linear alkyl group having 10 to 22 carbon atoms and x=0 or 1 to 16,
acyl sarcosides having 10 to 18 carbon atoms in the acyl group,
acyl taurides having 10 to 18 carbon atoms in the acyl group,
acyl isethionates having 10 to 18 carbon atoms in the acyl group,
sulfosuccinic mono- and dialkyl esters having 8 to 18 carbon atoms in the alkyl group and sulfosuccinic monoalkylpolyoxyethyl esters having 8 to 18 carbon atoms in the alkyl group and 1 to 6 oxyethyl groups,
linear alkanesulfonates having 12 to 18 carbon atoms,
linear alpha-olefinsulfonates having 12 to 18 carbon atoms,
alpha-sulfofatty acid methyl esters of fatty acids having 12 to 18 carbon atoms,
alkyl sulfates and alkylpolyglycol ether sulfates of the formula R—O—($CH_2$—$CH_2O)_x$—$SO_3H$, in which R is a preferably linear alkyl group having 10 to 18 carbon atoms and x=0 or 1 to 12,
mixtures of surface-active hydroxysulfonates according to DE-A-37 25 030,
sulfated hydroxyalkyl polyethylene and/or hydroxyalkylene propylene glycol ethers according to DE-A-37 23 354,
sulfonates of unsaturated fatty acids having 12 to 24 carbon atoms and 1 to 6 double bonds according to DE-A-39 26 344, esters of tartaric acid and citric acid with alcohols, which constitute addition products of about 2–15 molecules of ethylene oxide and/or propylene oxide onto fatty alcohols having 8 to 22 carbon atoms.

Preferred anionic surfactants are alkyl sulfates, alkylpolyglycol ether sulfates and ether carboxylic acids having 10 to 18 carbon atoms in the alkyl group and up to 12 glycol ether groups in the molecule, and in particular salts of saturated and in particular unsaturated $C_8$–$C_{22}$-carboxylic acids, such as oleic acid, stearic acid, isostearic acid and palmitic acid.

Nonionogenic surfactants comprise, as hydrophilic group, e.g. a polyol group, a polyalkylene glycol ether group or a combination of polyol and polyglycol ether group. Such compounds are, for example, addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group, $C_{12}$–$C_{22}$-fatty acid mono- and diesters of addition products of from 1 to 30 mol of ethylene oxide onto glycerol, $C_8$–$C_{22}$-alkylmono- and oligoglycosides and ethoxylated analogs thereof, and addition products of from 5 to 60 mol of ethylene oxide onto castor oil and hydrogenated castor oil.

Preferred nonionic surfactants are alkyl polyglycosides of the general formula $R^1O$-$(Z)_x$. These compounds are characterized by the following parameters.

The alkyl radical $R^1$ comprises 6 to 22 carbon atoms and can either be linear or branched. Preference is given to primary linear and 2-position methyl-branched aliphatic radicals. Such alkyl radicals are, for example, 1-octyl, 1-decyl, 1-lauryl, 1-myristyl, 1-cetyl and 1-stearyl. Particular preference is given to 1-octyl, 1-decyl, 1-lauryl, 1-myristyl. If so-called oxo alcohols are used as starting materials, compounds with an uneven number of carbon atoms in the alkyl chain predominate.

The alkyl polyglycosides which can be used according to the invention can comprise, for example, only a specific alkyl radical $R^1$. Usually, these compounds, however, are prepared starting from natural fats and oils or mineral oils. In this case, the alkyl radicals R present are mixtures corresponding to the starting compounds or corresponding to the particular work-up of these compounds.

Particular preference is given to those alkyl polyglycosides in which $R^1$ consists essentially of $C_8$- and $C_{10}$-alkyl groups,
essentially of $C_{12}$- and $C_{14}$-alkyl groups,
essentially of $C_8$–$C_{16}$-alkyl groups or
essentially of $C_{12}$–$C_{16}$-alkyl groups.

The sugar building block Z which may be used is any mono- or oligosaccharides. Usually, sugars with 5 or 6 carbon atoms, and the corresponding oligosaccharides are used. Such sugars are, for example, glucose, fructose, galactose, arabinose, ribose, xylose, lyxose, allose, altrose, mannose, gulose, idose, talose and sucrose. Preferred sugar building blocks are glucose, fructose, galactose, arabinose and sucrose; glucose is particularly preferred.

The alkyl polyglycosides which can be used according to the invention comprise, on average, 1.1 to 5 sugar units. Alkyl polyglycosides with x values of from 1.1 to 1.6 are preferred. Very particular preference is given to alkyl glycosides in which x is 1.1 to 1.4.

Besides their surfactant effect, the alkyl glycosides also serve to improve the fixing of scent components on the hair. Thus, when it is desirable for the effect of the perfume oil on the hair to last beyond the hair treatment, the person skilled in the art will preferably have recourse to this class of substances as a further ingredient of the preparations according to the invention.

The alkoxylated homologs of the specified alkyl polyglycosides can also be used according to the invention. These homologs can, on average, comprise up to 10 ethylene oxide and/or propylene oxide units per alkyl glycoside unit.

It is also possible to use zwitterionic surfactants, in particular as cosurfactants. Zwitterionic surfactants is the term used for those surface-active compounds which carry at least one quaternary ammonium group and at least one —$COO^{(-)}$ or —$SO_3^{(-)}$ group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethyl hydroxyethylcarboxymethyl glycinate. A preferred zwitterionic surfactant is the fatty acid amide derivative known under the INCI name Cocamidopropyl Betaine.

Likewise suitable in particular as cosurfactants are ampholytic surfactants. Ampholytic surfactants are understood as meaning those surface-active compounds which, apart from a $C_8$–$C_{18}$-alkyl or acyl group in the molecule, comprise at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12-18}$-acylsarcosine.

The cationic surfactants used according to the invention are, in particular those of the quaternary ammonium compound type, the esterquat type and the amidoamine type.

Preferred quaternary ammonium compounds are ammonium halides, in particular chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, and the imidazolium compounds known under the INCI names Quaternium-27 and Quaternium-83. The long alkyl chains of the abovementioned surfactants preferably have 10 to 18 carbon atoms.

Ester quats are known substances which comprise both at least one ester function and also at least one quaternary ammonium group as structural element. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the trade names Stepantex®, Dehyquart® and Armocare®. The products Armocare® VGH-70, an N,N-bis(2-palmitoyloxyethyl)dimethylammonium chloride, and Dehyquart® F-75 and Dehyquart® AU-35 are examples of such ester quats.

The alkylamidoamines are usually prepared by amidation of natural or synthetic fatty acids and fatty acid cuts with dialkylaminoamines. A further compound suitable according to the invention from this group of substances is the stearamidopropyldimethylamine commercially available under the name Tegoamid® S 18.

Further cationic surfactants which can be used according to the invention are the quaternized protein hydrolyzates.

Likewise suitable according to the invention are cationic silicone oils, such as, for example, the commercially available products Q2-7224 (manufacturer: Dow Corning; a stabilized trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, Quaternium-80).

One example of a quaternary sugar derivative which can be used as cationic surfactant is the commercial product Glucquat® 100, according to INCI nomenclature a "Lauryl Methyl Gluceth-10 Hydroxypropyl Dimonium Chloride".

The compounds with alkyl groups used as surfactant may in each case be uniform substances. However, it is usually preferred when producing these substances to start from native vegetable or animal raw materials, thus giving rise to mixtures of substances with varying alkyl chain lengths dependent on the particular raw material.

In the case of the surfactants which constitute addition products of ethylene oxide and/or propylene oxide onto fatty alcohols or derivatives of these addition products it is possible to use either products with a "normal" homolog distribution or those with a narrowed homolog distribution. In this connection, "normal" homolog distribution is understood as meaning mixtures of homologs which are obtained during the reaction of fatty alcohol and alkylene oxide using alkali metals, alkali metal hydroxides or alkali metal alkoxides as catalysts. Narrowed homolog distributions are, by contrast, obtained if, for example, hydrotalcites, alkaline earth metal salts of ether carboxylic acids, alkaline earth metal oxides, hydroxides or alkoxides are used as catalysts. The use of products with a narrowed homolog distribution may be preferred.

In addition, the colorants according to the invention can comprise further active ingredients, auxiliaries and additives, such as, for example, nonionic polymers, such as, for example, vinylpyrrolidone/vinyl acrylate copolymers, polyvinylpyrrolidone and vinylpyrrolidone/vinyl acetate copolymers and polysiloxanes, cationic polymers, such as quaternized cellulose ethers, polysiloxanes with quaternary groups, dimethyldiallylammonium chloride polymers, acrylamide-dimethyldiallylammonium chloride copolymers, dimethylaminoethyl methacrylate-vinylpyrrolidone copolymers quaternized with diethyl sulfate, vinylpyrrolidone-imidazolinium methochloride copolymers and quaternized polyvinyl alcohol, zwitterionic and amphoteric polymers, such as, for example, acrylamidopropyltrimethylammonium chloride/acrylate copolymers and octylacrylamide/methyl methacrylate/tert-butylaminoethyl methacrylate/2-hydroxypropyl methacrylate copolymers, anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers, thickeners, such as agar agar, guar gum, alginates, xanthan gum, gum arabic, karaya gum, carob seed flour, linseed gums, dextrans, cellulose derivatives, e.g. methylcellulose, hydroxyalkylcellulose and carboxymethylcellulose, starch fractions and derivatives, such as amylose, amylopectin and dextrins, clays, such as, for example, bentonite or completely synthetic hydrocolloids, such as, for example, polyvinyl alcohol, structurants, such as maleic acid and lactic acid, hair-conditioning compounds, such as phospholipids, for example soya lecithin, egg lecithin and cephalins, protein hydrolyzates, in particular elastin, collagen, keratin, milk protein, soya protein and wheat protein hydrolyzates, their condensation products with fatty acids, and quaternized protein hydrolyzates, perfume oils, dimethyl isosorbide and cyclodextrins, solvents and solubility promoters, such as ethanol, isopropanol, ethylene glycol, propylene glycol, glycerol and diethylene glycol, fiber-structure-improving active ingredients, in particular mono-, di- and oligosaccharides, such as, for example, glucose, galactose, fructose, fruit sugars and lactose, quaternized amines, such as methyl-1-alkylamidoethyl-2-alkylimidazolinium methosulfate antifoams, such as silicones, dyes for coloring the composition, antidandruff active ingredients, such as piroctone olamine, zinc omadine and climbazole, photoprotective agents, in particular derivatized benzophenones, cinnamic acid derivatives and triazines, substances for adjusting the pH, such as, for example, customary acids, in particular food acids and bases, active ingredients, such as allantoin, pyrrolidonecarboxylic acids and salts thereof, and bisabolol, vitamins, provitamins and vitamin precursors, in particular those of groups A, $B_3$, $B_5$, $B_6$, C, E, F and H, plant extracts, such as the extracts from green tea, oak bark, stinging nettle, hamamelis, hops, camomile, burdock, horsetail, hawthorn, linden blossom, almond, aloe vera, fir needle, roast chestnut, sandalwood, juniper, coconut, mango, apricot, lemon, wheat, kiwi, melon, orange, grapefruit, sage, rosemary, birch, mallow, lady's smock, wild thyme, yarrow, thyme, melissa, restharrow, coltsfoot, marshmallow, meristem, ginseng and ginger root, cholesterol, consistency regulators, such as sugar esters, polyol esters and polyol alkyl ethers, fats and waxes, such as spermaceti, beeswax, montan wax and paraffins, fatty acid alkanolamides, complexing agents, such as EDTA, NTA, β-alaninediacetic acid and phosphonic acids, swelling and penetration substances, such as glycerol, propylene glycol monoethyl ether, carbonates, hydrogencarbonates, guanidines, ureas, and primary, secondary and tertiary phosphates, opacifiers, such as latex, styrene/PVP and styrene/acrylamide copolymers pearlizing agents, such as ethylene glycol mono- and distearate, and PEG-3 distearate, pigments, stabilizers for hydrogen peroxide and other oxidizing agents, propellants, such as propane-butane mixtures, $N_2O$, dimethyl ether, $CO_2$ and air, antioxidants.

With regard to further optional components and to the amounts of these components used, reference is made expressly to the relevant handbooks known to the person skilled in the art, e.g. Kh. Schrader, Grundlagen und Rezepturen der Kosmetika [Fundamentals and formulations of cosmetics], 2nd edition, Hüthig Buch Verlag, Heidelberg, 1989.

The actual oxidative coloring of the fibers can in principle take place with atmospheric oxygen. However, preference is given to using a chemical oxidizing agent, particularly if a lightening effect on human hair is desired besides the coloring. Suitable oxidizing agents are persulfates, chlorites and, in particular, hydrogen peroxide or its addition products onto urea, melamine and sodium borate. However, according to the invention, the oxidation colorant can also be applied to the hair together with a catalyst which activates the oxidation of the dye precursors, e.g. by atmospheric oxygen. Such catalysts are, for example, metal ions, iodides, quinones or certain enzymes.

Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. Of particular suitability in this connection are $Zn^{2+}$, $Cu^{2+}$ and $Mn^{2+}$. The metal ions can in principle be used in the form of any physiologically compatible salt or in the form of a complex compound. Preferred salts are the acetates, sulfates, halides, lactates and tartrates. The use of these metal salts can both accelerate the development of the coloration and also influence the color nuance in a targeted manner.

Suitable enzymes are, for example, peroxidases, which can considerably enhance the effect of small amounts of hydrogen peroxide. Also of suitability according to the invention are those enzymes which directly oxidize the oxidation dye precursors with the help of atmospheric oxygen, such as, for example, the laccases, or produce in situ small amounts of hydrogen peroxide and in so doing biocatalytically activate the oxidation of the dye precursors. Particularly suitable catalysts for the oxidation of the dye precursors are the so-called 2-electron oxidoreductases in combination with the substrates specific therefor, e.g.

pyranose oxidase and e.g. D-glucose or galactose, glucose oxidase and D-glucose, glycerol oxidase and glycerol, pyruvate oxidase and pyruvic acid or salts thereof, alcohol oxidase and alcohol (MeOH, EtOH), lactate oxidase and lactic acid and salts thereof, tyrosinase oxidase and tyrosine, uricase and uric acid or salts thereof, choline oxidase and choline, amino acid oxidase and amino acids.

The surface of the film sachet is given an embossed structure by heating and pressing, preferably prior to filling the film sachet with a cosmetic preparation.

The coating material is preferably a blow-molded or, in particular, cast polymer film which is embossed in the heated state using a die in order to impart the advantageous surface properties to it. The embossing operation is preferably carried out in such a way that the film is pressed on one side with the die tool so that a three-dimensional structure is embossed on one side and appears again on the opposite side as a "negative".

The portions according to the invention are usually marketed in a selling unit (kit) containing a mixing set and optionally one or more further preparations and/or cosmetic applications devices. The present embodiment according to the invention thus further provides a kit comprising a mixing set and one or more portions according to the invention.

In a further advantageous embodiment, the kit according to the invention additionally comprises one or more constituents chosen from the group a) one or more further receiving container(s) comprising at least one further cosmetic preparation, preferably a hydrogen peroxide solution or hydrogen peroxide emulsion or a care lotion; and/or b) one or more safety materials for avoiding the undesired contact between the cosmetic preparation and the human body, preferably gloves.

In a particularly advantageous embodiment, the mixing set according to the invention comprises at least one portion according to the invention with a bleaching powder as preparation, a mixing device, and preferably a plastic bottle containing an aqueous hydrogen peroxide solution or hydrogen peroxide emulsion or hydrogen peroxide dispersion and optionally additionally a care lotion.

In a further advantageous embodiment, the kit according to the invention comprises at least one or more portions according to the invention which comprise bleaching powder as cosmetic preparation, one or more containers comprising a hydrogen peroxide emulsion or hydrogen peroxide dispersion, a mixing device for mixing the components, and safety gloves and optionally one or more highlighting caps or highlighting needles.

In a further advantageous embodiment of the invention, the kit according to the invention comprises at least one or more portions according to the invention comprising a hair colorant, preferably a hair colorant precursor, particularly advantageously component A of an oxo colorant. In addition, the kit comprises a mixing device for mixing the components and preferably additionally one or more portions comprising a further hair coloring component, preferably component B of an oxo colorant and optionally additionally an oxidizing agent preparation (C), which can either be aqueous, e.g. in the case of hydrogen peroxide or in the form of an anhydrous powder, e.g. a hydrogen peroxide adduct onto urea (percarbamide) or onto melamine (melamine perhydrate) or in the form of another percompound, e.g. magnesium peroxide or potassium persulfate.

A further subject-matter is the use of the above-described water-soluble and/or water-dispersible film sachets for portioning cosmetic preparations. The surface of the film sachet has, as already described, a square mean value for the roughness of at least 10 µm. For the purposes of the present embodiment according to the invention, portioning is understood as meaning the dividing of quantitative amounts into suitable handleable sizes, e.g. the amount required for a single hair-coloring or hair-bleaching operation. These quantity units are packaged by means of the coating material to give portions, e.g. to give water-soluble sachets or capsules.

A further subject-matter is the use of a water-soluble and/or water-dispersible film sachet for the portioning of cosmetic preparations which preferably have the roughness values described above. The use takes place in the course of this subject-matter with a coating which has a three-dimensional macroscopic surface which is at least 10%, advantageously at least 20%, further advantageously at least 30% and 50%, larger than the two-dimensional geometric surface.

BRIEF DESCRIPTION OF THE DRAWINGS

The invention is explained in more detail by way of example below by reference to the drawing and working examples. This shows, in each case in a longitudinal section.

DETAILED DESCRIPTION OF THE INVENTION

Figure 1:
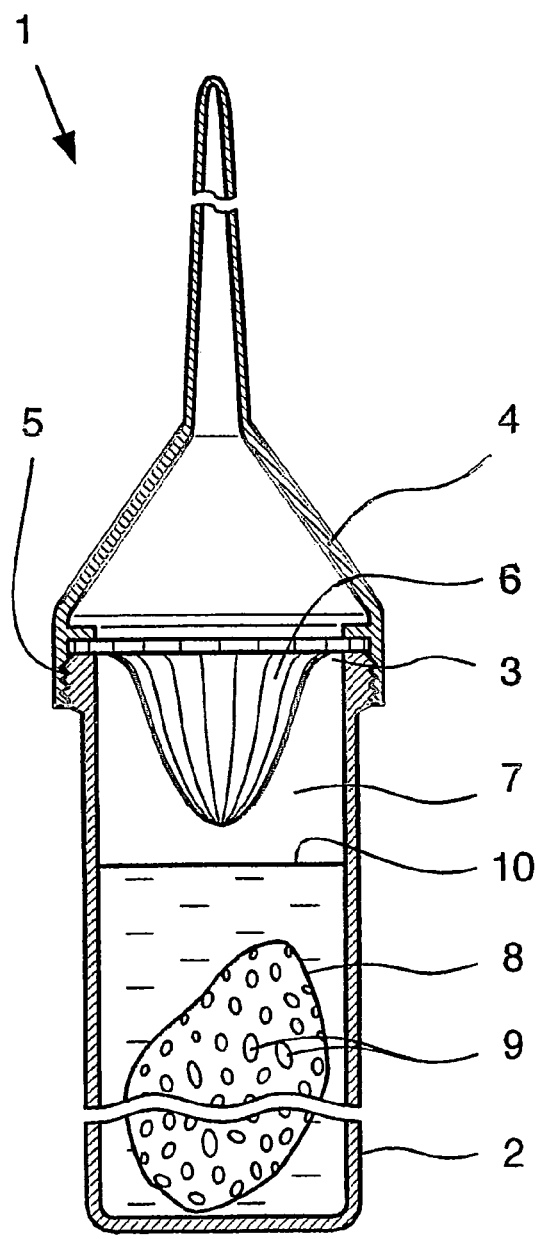
FIG. 1 a mixing device according to a first configuration.

A mixing device according to the invention is generally indicated in the drawing by 1. This mixing device 1 has a mixing container 2 which is provided on the upper side with a container opening 3 which can be sealed with a container lid 4, where in the case of the working example the container lid 4 can be screwed on; a screw thread is indicated by 5.

As alternatives to the screw connection, a plug connection or a snap-action latch may also be provided.

In the region of the container opening 3, an insert 6 is placed on the container 2; this is curved out like a citrus press into the receiving chamber 7 of the container. This insert 6 can be removed from the container opening in order to fill the receiving chamber of the container 7, then it can be replaced and then remains firmly positioned after the container lid 4 has been screwed on.

The mixing device 1 designed in this way serves to receive a product 9 contained in a film sachet 8 which is soluble in a liquid solvent, said product preferably being a bleaching powder.

Besides the film sachet 8 filled with the product 9, a liquid solvent which is able to dissolve the film sachet 8 is introduced into the receiving chamber 7 with an opened mixing container 2. This liquid solvent is, for example, a hydrogen peroxide solution. This is introduced from a receiving container which is not shown into the receiving chamber 7 of the mixing container 2. Moreover, a further component, for example a bleaching cream, can also additionally be introduced from a likewise not shown further receiving container into the receiving chamber 7.

The citrus press-like insert 6 is then placed onto the container opening 3 and the container opening 3 is closed with the lid 4. If the mixing device 1 is now shaken by the user, the film sachet 8 automatically comes into contact with the citrus press-like insert 6 and in so doing becomes mechanically strained to such an extent that it tears, at least in places. The pulverulent product 9 can then escape directly from the film sachet and mix with the liquid, the fill level for which in the resting state is indicated by 10. As a result, the rate of the mixing operation is increased significantly, and, moreover, as a result of the comminution or disruption of the film sachet 8, the latter can also be dissolved more quickly by the liquid solvent. After an adequate mixing time, which depends on the products to be mixed, the mixing container 2 is opened again by removing the lid 4. The insert 6 is then removed and the finished product can be taken out.

Figure 2:
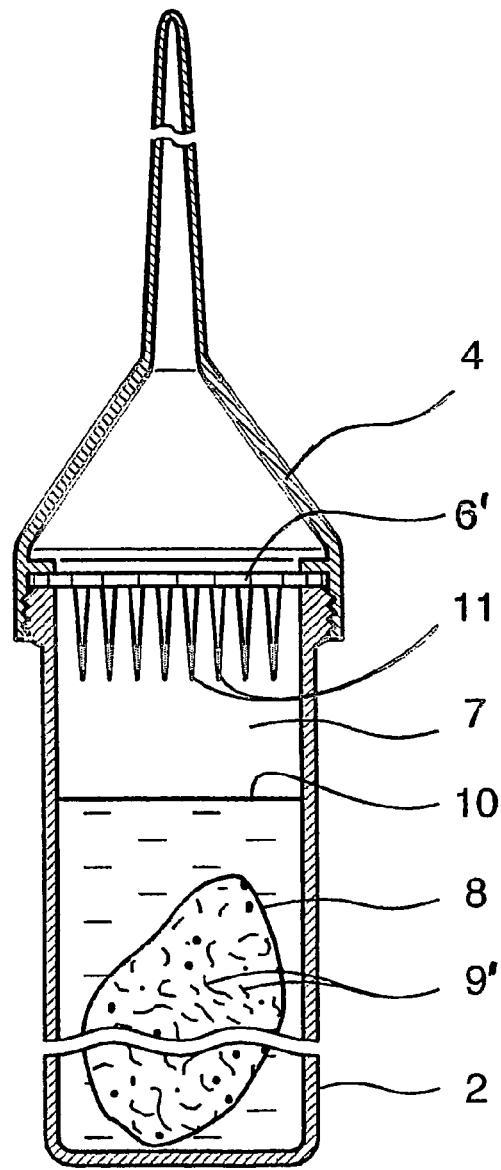
FIG. 2 a mixing device according to a second configuration.

The embodiment according to FIG. 2 differs from that according to FIG. 1 only by virtue of a differently designed insert 6'. This insert 6' is constructed like a sieve plate and is provided with tapered pins 11 pointing into the receiving chamber 7.

Upon shaking the mixing device, the pins 11 penetrate into at least some areas of the film sachet 8 and lead to its partial destruction, meaning that the pulverulent product 9 can escape easily and mix with the liquid solvent.

The invention is of course not limited to the working examples shown. Further configurations are possible without departing from the basic concept. For example, instead of the inserts shown, it is also possible for other internal inserts to be provided for the mechanical action on the film sachet in the receiving chamber; these may also be arranged in a fixed manner within the receiving chamber.

Furthermore, an additional liquid-tight cover can also be attached above the inserts which prevents liquid passing into the space above the inserts during the mixing operation. This cover is then removed together with the inserts when the mixing operation is complete.

Alternatively, it is to be provided that the insert and the lid consist of a single element, which can be produced, for example, in an injection molding process.

As design simplest for the user, such a single-part design is also firmly attached to a seal configured as a sealing ring. In this simplest case, the closure required for using the mixing container requires only a single hand grip.

Moreover, the film sachet can be under superatmospheric pressure, which also informs the user acoustically of the destruction as a result of the mechanical strain by the internal inserts. After the expected pop, it can be assumed that the sachet is torn at least in some areas, and thus the contained product is ready for the mixing operation.

In a further advantageous case, the product contained in the film sachet is a cosmetic preparation and the two together form a cosmetic portion.

Examples of the cosmetic portion:

EXAMPLE 1

A portion according to the invention comprising a bleaching powder with the composition given in Table 1 was prepared.

TABLE 1

| Bleaching powder | |
|---|---|
| Raw material | Data in % by wt. |
| Ammonium persulfate | 21.5% |
| Sodium phosphate | 4.0% |
| Aerosil 200 | 3.0% |
| Potassium persulfate | 33.0% |
| Britesil ® C 20 | 22.0% |
| Sodium stearate | 8.0% |
| Ceasit ® I | 4.0% |
| Magnesium oxide | 2.0% |
| Magnesium hydroxide carbonate | 1.0% |
| Lanette ® E | 1.0% |
| Idranal ® III | 0.5% |

The following raw materials were used:
Aerosil® 200: fumed silica (INCI name: Silica) (Degussa)
Britesil® C20: sodium silicate; molar ratio $SiO_2:Na_2O=2.0$
Ceasit® I: calcium stearate
Lanette®E: sodium cetylstearyl sulfate (ex Cognis)
Idranal® III: ethylenediamine-N,N,N',N'-tetraacetic acid disodium salt The raw material components of the bleaching powder are mixed and ground until the average particle size is 100 μm.

The bleaching powder is then packaged in a water-soluble PVA polymer film (Solublon, type SA 20 ex Syntana) using a tubular sachet sealing process.

The film sachet has the following properties:
square mean value for the
roughness: 30 μm
average thickness of the film: 20 μm
film material: partially hydrolyzed polyvinyl acetate with a degree of hydrolysis of 96%; cast film; average molecular weight: 36 000 g/mol The outer and inner surfaces of the polymer film have a three-dimensional structure with a square-shaped pattern. The pattern is formed by a grid with square indentations, meaning that the grid lines are formed by the edges of the indentations.

The depth of the indentation is 0.12 mm. The embossed squares have a diameter of 0.6 mm.

The portion according to the invention comprises 25 g of the abovementioned bleaching powder.

The portion was subsequently dissolved in a hydrogen peroxide dispersion with a composition according to Table 2, at 20° C.:

TABLE 2

Hydrogen peroxide dispersion

| Raw materials | Data in % by wt |
|---|---|
| Lorol ® C16 | 3.6% |
| Eumulgin | 0.9% |
| Texapon ® NSO | 2.25% |
| Ammonia (25%) | 0.65% |
| Dipicolinic acid | 0.1% |
| Sodium pyrophosphate | 0.03% |
| Turpinal ® SL | 1.5% |
| Hydrogen peroxide | 6% |
| Water | ad 100% |

The following raw material components were used:
Lorol® $C_{16}$: $C_{16}$-fatty alcohol
Eumulgin®: Ceteareth-20
Texapon® NSO: sodium lauryl ether sulfate with 2 EO
Turpinal® SL: hydroxyethyldiphosphonic acid It has been found that the portion according to the invention dissolves about 5 times as quickly as the portions known from the prior art with coating materials made of smooth water-soluble films of comparable thicknesses.

The portion according to the invention is contained in a kit together with the following constituents:
a) a mixing device
c) a plastic bottle containing a hydrogen peroxide dispersion according to Table 2
d) a conditioner

EXAMPLE 2

Formulation for the Oxo Coloring

Coloring with CH-acidic components and aromatic aldehyde

TABLE 3

| Component 1 | | Component 2 | |
|---|---|---|---|
| Paraffin oil, low-viscosity | 7.5 g | Cetiol ® B | 7.5 g |
| Cremophor ® RH 40 | 2.0 g | Dehydol ® LS3 | 4.0 g |
| Rheopearl ® KL | 0.5 g | Rheopearl ® KL | 0.5 g |

Both components (1 and 2) were heated to 80° C. with stirring. At this temperature, clear, low-viscosity liquids formed in both cases which, upon cooling to room temperature, thickened to give clear, medium-viscosity gels.

After cooling,
0.75 g of dimethylaminobenzaldehyde
1.2 g of Methocel® E4M and
0.5 g of arginine were homogeneously dispersed into component 1 and
0.85 g of 1,2-dihydro-1,3,4,6-tetramethyl-2-oxopyridinium chloride and
3.6 g of a $C_8$–$C_{10}$-fatty alcohol mixture liquid at room temperature (20° C.)
were homogeneously dispersed into component 2.

The following raw materials were used:
Cremophor RH 40: castor oil, hydrogenated with 40-45 ethylene oxide units (INCI name: PEG-40 Hydrogenated Castor Oil) (BASF)
Rheopearl®KL: dextrin palmitate ex Miyoshi Kasei
Cetiol® B: di-n-butyl adipate
Dehydol® LS 3: lauryl alcohol-3 EO ex Cognis
Methocel® E 4 M: hydroxypropylmethylcellulose To prepare a portion according to the invention, component 1 and component 2 were in each case introduced separately into a water-soluble film sachet which has the specification as in example 1, and then thermally sealed to be liquid-tight.

Portion 1 comprising component 1 and portion 2 comprising component 2 were stirred into 80 ml of water at 40° C. This gave a readily flowable emulsion.

A hair tress (Kerling natural white) colored with this formulation in the weight ratio 4:1 for 30 minutes at 32° C. was nuanced an intense magenta color.

EXAMPLE 3

Coloring with Oxidation Dyes

TABLE 4

| Paraffin oil, low-viscosity | 19.50 g |
|---|---|
| Dehydol ® LS4 | 0.25 g |
| Gelatinization agent GP-1 | 0.25 g |

The following raw material was used:
Gelatinization agent GP-1: N-lauroyl-1-glutamic acid-α,γ-di-n-butylamide ex Ajinomoto
Dehydol® LS4: lauryl alcohol-4 EO The gel was prepared as described in example 2 at 80° C. and cooling to room temperature. 1.2 g of tetraaminopyrimidine sulfate and 0.6 g of methylresorcinol and 2 g of sodium carbonate and 3 g of trisodium phosphate were homogeneously dispersed into the gel with the composition given in Table 4.

The gel was introduced into a film sachet with the coating material specified in example 1 and sealed to be liquid-tight analogously to example 2.

A 5 g portion was prepared which was mixed with 20 g of a commercial 6% strength developer emulsion (Poly Color cream hair color) and 20 g of a 2% strength Natrosol 250 HR swelling in which 0.5 g of ammonium sulfate were dissolved, at room temperature (20° C.).

This emulsion was used to dye a blond hair tress (Kerling natural white) (30 minutes, 32° C.). The nuancing of the tress was a luminous red.

The following raw materials were used:
Natrosol 250 HR: hydroxyethylcellulose ex Aqualon viscosity (1% in $H_2O$): 1.5–2.5 Pas (20° C.) viscosity (2% in $H_2O$): 30 Pas (20° C.)

EXAMPLE 4

Oxo Coloring

Coloring with Acidic Carbonyl Compounds and Aromatic Amines

TABLE 5

| Component 1 | | Component 2 | |
|---|---|---|---|
| Cetiol ® 868 (isooctyl stearate) | 2.00 g | Stenol ® 1618 | 4.00 g |
| | | Eumulgin B1 | 0.40 g |
| Paraffin oil, low-viscosity | 14.00 g | Eumulgin ® B2 | 0.40 g |
| | | p-tolylenediamine sulfate | 0.88 g |
| Cutina ® GMS | 2.00 g | ammonium sulfate | 0.20 g |
| Dehydol ® LS 2 | 2.00 g | water with ammonia to pH 9 | 34.12 g |

The following raw materials were used:
Dehydol® LS 2: lauryl alcohol-2 EO
Eumulgin® B2: cetylstearyl alcohol with 20 mol of ethylene oxide
Stenol® 1618: $C_{16}/C_{18}$-fatty alcohol mixture
Cutina® GMS: glycerol monostearate ex Cognis
Eumulgin® B1: cetylstearyl alcohol with 12 mol of ethylene oxide The constituents of component 1 were heated to 80° C. 0.6 g of N-allylisatin was dissolved in the hot mixture. Then, with stirring, the mixture was cooled to room temperature. The formulation was packaged in a tubular sachet as in example 2. After dissolving the portion in component 2, the coloring of a blond hair tress (Kerling natural white, 30 minutes, 32° C.) was carried out. The color of the tress was titian red.

The invention claimed is:

1. A combination film sachet and a mixing device for mixing a product or the like, which is contained in a film sachet, wherein the film sachet is soluble in a mixing component that is a liquid solvent, the mixing device comprising a sealable mixing container having a receiving chamber for receiving the product contained in the film sachet and with the mixing component, with the film sachet being disposed in the receiving chamber and an internal insert for the mechanical disruption of the film sachet in the receiving chamber.

2. The mixing device according to claim 1, wherein the mixing container has a container opening and a removable lid for sealing the opening.

3. The mixing device according to claim 2, wherein the internal insert is mounted adjacent the container opening.

4. The mixing device according to claim 3, wherein the insert is firmly joined to the lid.

5. The mixing device according to claim 1 including a seal at the top of the insert.

6. The mixing device according to claim 1, wherein the insert comprises a curved out portion in the form of a citrus press which projects into the receiving chamber.

7. The mixing device according to claim 1, wherein the internal insert comprises a sieve plate with at least one tapered pin or spike pointing into the receiving chamber.

8. The mixing device according to claim 1, wherein the internal insert comprises knife-like spike elements pointing into the receiving chamber.

9. A mixing kit having
a) a mixing device comprising a sealable mixing container having a receiving chamber for a product contained in a film sachet and for a mixing component, and an internal insert for the mechanical disruption of the film sachet in the receiving chamber,
b) a product contained in a film sachet wherein the film sachet is soluble in a liquid solvent, and
c) a mixing component comprising the liquid solvent.

10. The mixing kit according to claim 9, wherein the product is in a form selected from a group consisting of powders, granules, pastes, gels, liquids, and tablets.

11. The mixing kit according to claim 9, wherein the surface of the film sachet has a square mean roughness value of at least 10 µm.

12. The mixing kit according to claim 9, wherein the surface of the film sachet has a three-dimensional macroscopic surface in one portion and a two-dimensional geometric surface in another portion, the three-dimensional macroscopic surface being at least 10% larger than the two-dimensional geometric surface.

13. The mixing kit according to claim 12, wherein the three-dimensional macroscopic surface has an embossed coating with a three-dimensional structure.

14. The mixing kit according to claim 9, wherein the film of the sachet is constructed of a material that comprises means for dissolving completely in water at 20° C. in less than 5 minutes.

15. The mixing kit according to claim 9, wherein the product is a cosmetic and the mixing component comprises a bleaching agent.

16. The mixing kit according to claim 9, wherein the sachet is in a sealed—closed condition and pressurized to a pressure greater than atmospheric pressure.

17. A method of preparing a mixture of a product with at a mixing component comprising the steps of:
a) providing a mixing device comprising a sealable mixing container having a receiving chamber for a product contained in the film sachet and a mixing component, and an internal insert for the mechanical disruption of the film sachet in the receiving chamber,
b) providing a product contained in a film sachet wherein the film sachet is soluble in a liquid solvent, and providing a mixing component comprising the liquid solvent,
c) inserting the sachet into the receiving chamber, and adding the mixing component into the chamber, and closing said chamber with a lid,
d) agitating said mixing device to cause said internal insert to mechanically disrupt the film of said sachet and expose the product to the mixing component, and
e) continuing said agitation until said liquid solvent dissolves said film.

18. The method of preparing a mixture of a product with a mixing component according to claim 17 including the step of opening said chamber after mechanically disrupting said film and removing said internal insert from said chamber.

19. The method of preparing a mixture of a product with a mixing component according to claim 17 including the step of adding an additional component to said mixing component before closing said container.

20. The method of preparing a mixture of a product with at a mixing component according to claim 17 wherein the step b) includes pressurizing the sachet to a pressure greater than atmospheric pressure.

* * * * *